US011881306B2

(12) United States Patent
Bohn et al.

(10) Patent No.: US 11,881,306 B2
(45) Date of Patent: Jan. 23, 2024

(54) SYSTEM AND METHOD OF UTILIZING DATA OF MEDICAL SYSTEMS

(71) Applicant: Alcon Inc., Fribourg (CH)

(72) Inventors: Heiko Bohn, Nuremberg (DE); Peter Martin, Velden (DE)

(73) Assignee: Alcon Inc., Fribourg (CH)

(*) Notice: Subject to any disclaimer, the term of this patent is extended or adjusted under 35 U.S.C. 154(b) by 795 days.

(21) Appl. No.: 16/815,343

(22) Filed: Mar. 11, 2020

(65) Prior Publication Data

US 2020/0312447 A1 Oct. 1, 2020

Related U.S. Application Data

(60) Provisional application No. 62/824,642, filed on Mar. 27, 2019.

(51) Int. Cl.

| | |
|---|---|
| ***G16H 40/40*** | (2018.01) |
| ***G16H 40/20*** | (2018.01) |
| ***G06K 7/10*** | (2006.01) |
| ***G06K 7/14*** | (2006.01) |
| ***G06N 3/08*** | (2023.01) |
| ***G06Q 10/0631*** | (2023.01) |

(52) U.S. Cl.
CPC ......... *G16H 40/40* (2018.01); *G06K 7/10366* (2013.01); *G06K 7/1413* (2013.01); *G06N 3/08* (2013.01); *G06Q 10/063112* (2013.01); *G06Q 10/063114* (2013.01); *G16H 40/20* (2018.01)

(58) Field of Classification Search
None
See application file for complete search history.

(56) References Cited

U.S. PATENT DOCUMENTS

| | | | | |
|---|---|---|---|---|
| 2011/0121969 A1 | | 5/2011 | Mercer | |
| 2019/0272475 A1* | | 9/2019 | Hegendoerfer | G06N 20/00 |
| 2020/0118675 A1* | | 4/2020 | Schriver | G16H 40/40 |

FOREIGN PATENT DOCUMENTS

| | | | | |
|---|---|---|---|---|
| EP | 0633536 A1 | 1/1995 | | |
| WO | WO-2019011765 A1 * | 1/2019 | | G06N 20/00 |
| WO | 2019028269 A2 | 2/2019 | | |

OTHER PUBLICATIONS

Gerald M. Knapp, Roya Javadpour, and Hsu-Pin (Ben) Wang. "An ARTMAP Neural Network-Based Machine Condition Monitoring System." Journal of Quality in Maintenance Engineering 6.2 (2000): 86-105. ProQuest. Web. Nov. 2, 2022. (Year: 2000).*

* cited by examiner

*Primary Examiner* — Lena Najarian

(57) ABSTRACT

The present disclosure provides a system that may receive first sensor data associated with first measurements of multiple components of respective multiple medical systems; may determine first one or more classifiers based at least on first user input; may receive second sensor data associated with second measurements of the multiple components; may determine, based at least on the first one or more classifiers and based at least on the second sensor data, at least two services to be provided to respective at least a first two of the multiple medical systems; may receive third sensor data associated with third measurements of multiple components respectively associated with the at least the first two of the multiple medical systems; and may determine, without the first user input and without second user input, second one or more classifiers based at least on the third sensor data.

18 Claims, 14 Drawing Sheets

SYSTEM AND METHOD OF UTILIZING DATA OF MEDICAL SYSTEMS

BACKGROUND

Field of the Disclosure

This disclosure relates to medical systems utilized in medical procedures and more particularly to utilizing data of the medical systems.

Description of the Related Art

Medical systems can be utilized in medical procedures. A medical system includes sensors that monitor various components of the medical system. The data from the sensors is stored by a computer system of the medical system. A technician that provides service to the medical system can access the computer system of the medical system and the data stored. However, the technician has to travel to a location that utilizes the medical system. This consumes response time if there is an issue associated with the medical system. In one case, there can be a malfunction with the medical system. In another case, there can be a preventative maintenance issue with the medical system. Medical systems can require routine maintenance at various times.

SUMMARY

The present disclosure provides a system able to: receive first sensor data associated with first multiple measurements of multiple components of respective multiple medical systems; receive first user input that indicates one or more issues associated with at least one of the multiple medical systems; determine first one or more classifiers based at least on the first user input and based at least on the first sensor data; receive second sensor data associated with second multiple measurements of the multiple components of the respective multiple medical systems; and determine, based at least on the first one or more classifiers and based at least on the second sensor data, at least two services to be provided to respective at least a first two of the multiple medical systems. After the at least two services have been provided to the at least the first two of multiple medical systems, the system is further able to: receive third sensor data associated with third multiple measurements of multiple components respectively associated with the at least the first two of the multiple medical systems; determine, without the first user input and without second user input, second one or more classifiers based at least on the third sensor data; determine, based at least on the first one or more classifiers and based at least on the third sensor data, at least two services to be provided to respective at least two of the multiple medical systems; determine, based at least on the second one or more classifiers and based at least on the at least the second two services to be provided, multiple additional services to be respectively provided to the at least the second two of the multiple medical systems; and issue, to a computer system associated with a technician, a work order that includes at least one of the multiple additional services.

In one example, at least one of the second one or more classifiers may include a neural network. In a second example, at least one of the second one or more classifiers includes a k-nearest neighbor process. In a third example, at least one of the multiple additional services may include at least one preventative maintenance service. In a fourth example, the system is further able to: receive personnel information associated with a technician; determine, based at least on the personnel information associated with a technician, if the technician can provide service to at least one of the multiple medical systems; if the technician cannot provide service to the at least one of the multiple medical systems, provide, to a service manager, information that indicates that the technician cannot provide service to the at least one of the multiple medical systems; and if the technician can provide service to the at least one of the plurality of medical systems, provide, receive equipment identification information associated with equipment of the technician. In a fifth example, the system is further able to: determine, based at least on the equipment identification information, if the equipment of the technician can provide service to the at least one medical system of the multiple medical systems; if the equipment of the technician cannot provide service to the medical system, provide, to the service manager, information that indicates that the equipment cannot provide service to the at least one medical system of the multiple medical systems; and if the equipment of the technician can provide service to the medical system, provide, to the service manager, information that indicates that the service to the at least one medical system of the multiple medical systems has commenced. In another example, receiving the personnel information associated with the technician may include receiving at least one of a radio frequency identification (RFID) associated with the technician and a barcode associated with the technician.

A system may include multiple medical systems. The system may include multiple gateway devices coupled to the multiple medical systems. For example, a gateway device may include a network router configured to be coupled to at least one wide area network.

Each medical system of the multiple medical systems may include a first component and a first sensor that is configured to determined a first measurement of physical phenomena associated with the first component. Each medical system of the multiple medical systems may include a second component and a second sensor that is configured to determined a second measurement of physical phenomena associated with the second component. In one example, the first multiple measurements of the multiple components of the respective multiple medical systems may include each first measurement of the physical phenomena associated with each first component of each of the multiple medical systems. In a second example, the second multiple measurements of the multiple components of the respective multiple medical systems may include each second measurement of the physical phenomena associated with each second component of each of the multiple medical systems. Each medical system of the multiple medical systems may include a sensor hub. For example, the first sensor of each medical system of the multiple medical systems may be coupled to the sensor hub of the medical system. The sensor hub of each medical system of the multiple medical systems may be configured to receive data from the first sensor of the medical system via a first protocol and provide the data to a computer system of the medical system via a second protocol.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) receive first sensor data associated with first multiple measurements of multiple components of respective multiple medical systems; ii) receive first user input that indicates one or more issues associated with at least one of the multiple medical systems; iii) determine first one or more classifiers based at least on the first user input and based at least on the first sensor data; iv) receive second sensor data associated with second multiple measurements of the multiple components of the respective multiple medical systems; and determine, based at least on the first one or more classifiers and based at least on the second sensor data, at least two services to be provided to respective at least a first two of the multiple medical systems; v) receive third sensor data associated with third multiple measurements of multiple components respectively associated with the at least the first two of the multiple medical systems; vi) determine, without the first user input and without second user input, second one or more classifiers based at least on the third sensor data; vii) determine, based at least on the first one or more classifiers and based at least on the third sensor data, at least two services to be provided to respective at least two of the multiple medical systems; viii) determine, based at least on the second one or more classifiers and based at least on the at least the second two services to be provided, multiple additional services to be respectively provided to the at least the second two of the multiple medical systems; ix) issue, to a computer system associated with the technician, a work order that includes at least one of the multiple additional services; x) receive personnel information associated with the technician; xi) determine, based at least on the personnel information associated with a technician, if the technician can provide service to at least one of the multiple medical systems; xii) if the technician cannot provide service to the at least one of the multiple medical systems, provide, to a service manager, information that indicates that the technician cannot provide service to the at least one of the multiple medical systems; xiii) if the technician can provide service to the at least one of the multiple medical systems, receive equipment identification information associated with equipment of the technician; xiv) determine, based at least on the equipment identification information, if the equipment of the technician can provide service to the at least one medical system of the multiple medical systems; xv) if the equipment of the technician cannot provide service to the medical system, provide, to the service manager, information that indicates that the equipment cannot provide service to the at least one medical system of the multiple medical systems; and xvi) if the equipment of the technician can provide service to the medical system, provide, to the service manager, information that indicates that the service to the at least one medical system of the multiple medical systems has commenced.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1:
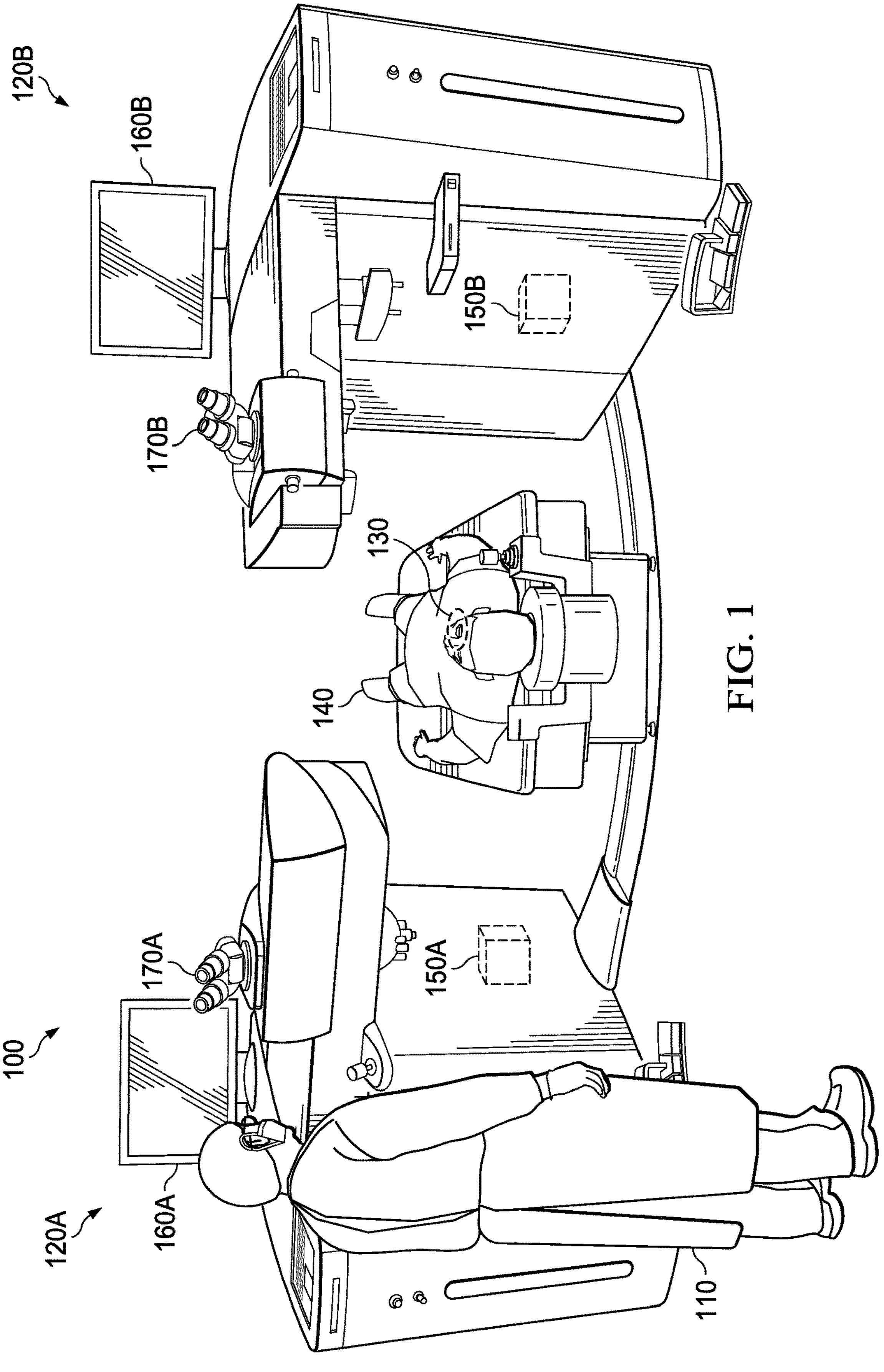
FIG. 1 illustrates an example of a system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

A surgeon may perform a medical procedure utilizing a medical system. For example, the medical procedure may be or include a surgery involving an eye of a patient. The surgery involving the eye of the patient may be or include a laser eye surgery. The laser eye surgery may be or include a laser vision correction (e.g., laser-assisted in situ keratomileusis (LASIK)). In one example, the medical system may control utilization of one or more medical instruments. In another example, the medical system may record utilization of the one or more medical instruments.

A computer system of the medical system may monitor sensors of the medical system. The computer system may receive and may store data from the sensors of the medical system. The computer system may store the data locally. The computer system may provide the data to another computer system. For example, the computer system may provide the data to a data center. The data center may be or may form part of a cloud computing solution and/or a cloud data storage solution.

The data may be analyzed. For example, the data may be analyzed to determine one or more issues. The one or more issues may include a deficient surgical technique, an inexperienced surgical technique, and/or one or more maintenance issues of one or more components of the medical system, among others. In one example, determining a level of skill in utilizing the medical system may be utilized in determining if an issue exists with the medical system. In a second example, one or more maintenance issues of one or more components of the medical system may include one or more preventative maintenance issues. In a third example, one or more maintenance issues of one or more components of the medical system may include one or more routine maintenance issues. In another example, one or more maintenance issues of one or more components of the medical system may include one or more malfunctions and/or one or more impairments associated with one or more components of the medical system.

One or more computer systems may be configured to utilize the data from the sensors of a medical system to determine one or more issues. For example, one or more computer systems may be configured to learn from the data from the sensors of a medical system to determine one or more issues. The one or more computer systems may be trained to determine one or more issues. For example, the one or more computer systems may be trained by the data from the sensors of a medical system and by user responses to the data from the sensors of the medical system. The one or more computer system may be trained to perform one or more actions. For example, the one or more computer systems may correlate data from sensors of a medical system and perform one or more actions based at least on the correlated data. The one or more action may include preventative and/or predictive maintenance, among others. For example, the one or more computer systems may issue service orders in performing the preventative and/or predictive maintenance, among others. A technician may receive a service order to complete a physical portion of the preventative and/or predictive maintenance, among others.

A service plan associated with the medical system may consume an amount of time. The service plan may include multiple processes. When maintenance is performed on the medical system, not all of the multiple processes may be performed. In one example, at least a first portion of the multiple processes may be performed in servicing the medical system. In another example, at least a second portion of the multiple processes may not be performed in servicing the medical system. One or more of the multiple processes of the service plan may include retrieving records (e.g., one or more log files) from the medical system. In one example, a technician (e.g., a person) may retrieve the records from the medical system. In a second example, the medical system may provide, via a network, the records to a computer system (e.g., a computer system of a datacenter). In another example, a computer system (e.g., a computer system of a datacenter) may retrieve, via a network, the records from the medical system. The one or more computer systems that have been trained may determine the at least the first portion of the multiple processes to be performed in servicing the medical system and/or may determine the at least the second portion of the multiple processes that may not be performed in servicing the medical system.

When a technician retrieves records from a medical system, one or more inaccuracies may be introduced into at least a portion of multiple processes associated with a service plan associated with the medical system. In one example, data may not be recorded correctly. In a second example, data may be interpreted incorrectly. In another example, data integrity may be compromised.

A medical system may record that one or more tools were utilized by a technician and/or when the technician performed maintenance on the medical system. In one example, at least one of the one or more tools that were utilized by the technician may be or include an incorrect tool. In a second example, at least one of the one or more tools that were utilized by the technician may have been utilized incorrectly. In a third example, at least one of the one or more tools that were utilized by the technician may be less efficient than another tool that could have been utilized. In a fourth example, at least one of the one or more tools that were utilized by the technician may not have been correctly calibrated. In a fifth example, at least one of the one or more tools that were utilized by the technician may not have been authorized for utilization by the technician. In another example, at least one of the one or more tools that were utilized by the technician may have been a correct tool. This may indicate that an issue after the performed maintenance on the medical system was not caused and/or was not induced by an incorrect tool. For example, one or more causes and/or one or more inducements may be eliminated in determining one or more issues subsequent to the performed maintenance on the medical system.

Utilizing the one or more computer systems that learn from the data from the sensors of respective medical systems to determine respective one or more issues may provide one or more advantages. In one example, an amount of time in providing service to a medical system may be reduced. In a second example, an amount of time in issuing a service order associated with a medical system may be reduced. In a third example, an amount of time that a medical system may be inoperable may be reduced. In a fourth example, one or more qualities of service of medical systems may be increased. In a sixth example, one or more compliances with one or more laws and/or one or more regulations may be achieved and/or ensured. In another example, one or more compliances with one or more standards may be achieved and/or ensured. By reducing one or more amounts of time associated with providing service to a medical system, issuing a service order associated with a medical system, an inoperability of a medical system, increasing one or more qualities of service of medical systems, complying with one or more laws, complying with one or more regulations, and/or complying with one or more standards, among others, may increase a number of patients that receive medical treatment and/or may increase one or more qualities of medical treatment that patients may receive.

Turning now to FIG. 1, an example of a system is illustrated. As shown, a surgeon 110 may utilize a medical system 100. For example, surgeon 110 may utilize system 100 in a surgery involving a patient portion 130 of a patient 140. System 100 may include multiple systems. As shown, system 100 may include a cutting system 120A. For example, surgeon 110 may utilize system 120A in cutting patient portion 130. Patient portion 130 may include a flap in a cornea of an eye of patient 140. As illustrated, system 100 may include a shaping system 120B. For example, surgeon 110 may utilize shaping system 120B in performing ablation on an interior part of the cornea of patient 140.

As shown, system 120A may include a display 160A. As illustrated, system 120A may include a microscope display 170A. For example, microscope display 170A may include a microscope integrated display (MID). As shown, system 120B may include a display 160B. As illustrated, system 120B may include a microscope display 170B. For example, microscope display 170B may include a MID.

System 120A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 160A and 170A, along with control devices and a computer system 150A. As shown, system 120A may include computer system 150A.

Systems 120A and 120B may be physically separated as shown in FIG. 1. Patient 140 may be moved between systems 120A and 120B. Alternatively, patient 140 may remain stationary and systems 120A and 120B may be moved to patient 140. Systems 120A and 120B may be physically combined into a single unitary device, such that neither the device nor patient 140 is repositioned when switching between systems 120A and 120B.

System 100 may include one or more control devices for controlling systems 120A and 120B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 100 may include includes at least one computer system configured to generate an image presented on at least one of displays 160A, 170A, 160B, and 170B, among others. For example, the at least one computer system may include one or more of computer systems 150A and 150B. One or more of computer systems 150A and 150B may be coupled to observational devices, such as a microscope, a camera, an optical coherence tomography (OCT) device or display, or another device able to measure the position of the eye undergoing surgery. One or more of computer systems 150A and 150B may be coupled to one or more of the control devices.

In one example, cutting device computer system 150A: i) may be coupled to observational devices that observe the eye when patient 140 is positioned with system 120A, ii) may provide graphical information regarding the planned flap location and the planned area of ablation to one or more of displays 160A and 170A, and iii) may be coupled to one or more control devices of system 120A. In a second example, shaping device computer 150B: i) may be coupled to observational devices that observe the eye when patient 140 is positioned with shaping device 130, ii) may provide graphical information regarding the planned flap location and the planned area of ablation to one or more of displays 160B and 170B, and iii) may be coupled to one or more control devices of system 120B. In another example, a computer system may include the properties and/or the attributes described above with respect to computer systems 150A and 150B.

A computer system of system 100 may be coupled to another part of system 100 in a wired fashion or in a wireless fashion. One of more of computer systems of system 100 may be coupled to a database, stored locally, on a remote computer system or a remote data center, or both that store patient data, treatments plans, or other information associated with medical treatments and/or system 100. In one example, the database may include a relational database. In a second example, the database may include a graph database. In another example, the database may include a "Not Only SQL" (NoSQL) database.

System 100 may enter information regarding a patient and the treatment to be performed on that patient or actually performed on that patient. System 100 may allow a user to enter and view information regarding a patient and the treatment to be performed on that patient. Such data may include information about the patient, such as identifying information, the patient's medical history, and information about patient portion 130 being treated. Such data may include information about the treatment plans, such as the shape and location of a corneal cut and a location and a degree of corneal ablation, among others.

Figure 2A:
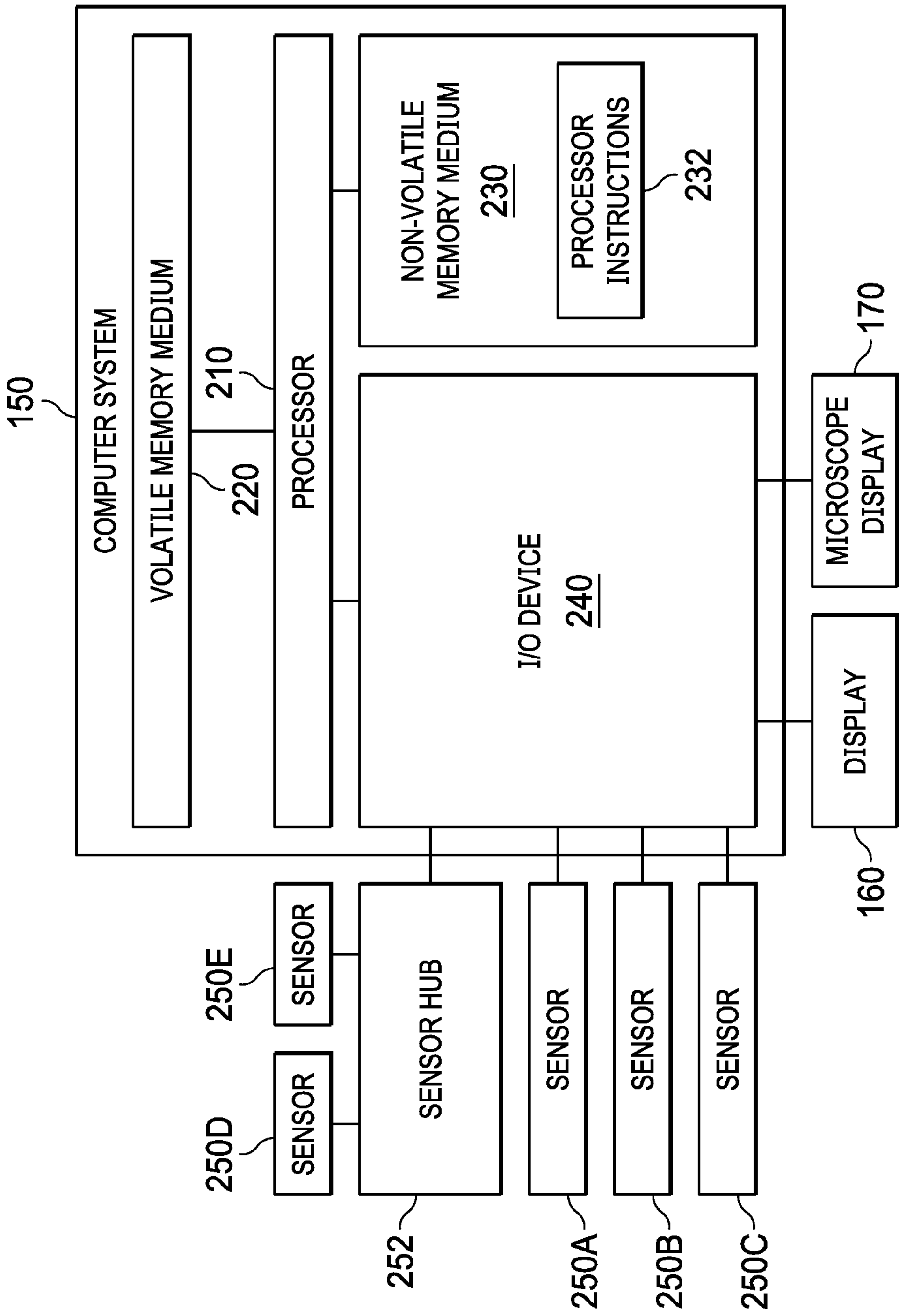
FIG. 2A illustrates an example of a computer system.

Turning now to FIG. 2A, an example of a computer system is illustrated. As shown, computer system 150 may include a processor 210, a volatile memory medium 220, a non-volatile memory medium 230, and an input/output (I/O) device 240. As illustrated, volatile memory medium 220, non-volatile memory medium 230, and I/O device 240 may be communicatively coupled to processor 210.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 230 may include processor instructions 232. Processor instructions 232 may be executed by processor 210. In one example, one or more portions of processor instructions 232 may be executed via non-volatile memory medium 230. In another example, one or more portions of processor instructions 232 may be executed via volatile memory medium 220. One or more portions of processor instructions 232 may be transferred to volatile memory medium 220.

Processor 210 may execute processor instructions 232 in implementing at least a portion of one or more systems, one or more flow charts, one or more processes, and/or one or more methods described herein. For example, processor instructions 232 may be configured, coded, and/or encoded with instructions in accordance with at least a portion of one or more systems, one or more flowcharts, one or more methods, and/or one or more processes described herein. Although processor 210 is illustrated as a single processor, processor 210 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 210 may include any suitable system, device, or apparatus operable to interpret and execute program instructions, process data, or both stored in a memory medium and/or received via a network. Processor 210 further may include one or more microprocessors, microcontrollers, digital signal processors (DSPs), application specific integrated circuits (ASICs), or other circuitry configured to interpret and execute program instructions, process data, or both.

I/O device 240 may include any instrumentality or instrumentalities, which allow, permit, and/or enable a user to interact with computer system 150 and its associated components by facilitating input from a user and output to a user. Facilitating input from a user may allow the user to manipulate and/or control computer system 150, and facilitating output to a user may allow computer system 150 to indicate effects of the user's manipulation and/or control. For example, I/O device 240 may allow a user to input data, instructions, or both into computer system 150, and otherwise manipulate and/or control computer system 150 and its associated components. I/O devices may include user interface devices, such as a keyboard, a mouse, a touch screen, a joystick, a handheld lens, a tool tracking device, a coordinate input device, or any other I/O device suitable to be used with a system, such as system 100.

I/O device 240 may include one or more busses, one or more serial devices, and/or one or more network interfaces, among others, that may facilitate and/or permit processor 210 to implement at least a portions of one or more systems, processes, and/or methods described herein. In one example, I/O device 240 may include a storage interface that may facilitate and/or permit processor 210 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 240 may include a network interface that may facilitate and/or permit processor 210 to communicate with a network. I/O device 240 may include one or more of a wireless network interface and a wired network interface. In a third example, I/O device 240 may include one or more of a peripheral component interconnect (PCI) interface, a PCI Express (PCIe) interface, a serial peripheral interconnect (SPI) interface, and an inter-integrated circuit ($I^2C$) interface, among others. In another example, I/O device 240 may facilitate and/or permit processor 210 to communicate data with one or more of display 160 and microscope display 170, among others.

As shown, I/O device 240 may be communicatively coupled to display 160 and microscope display 170. For example, computer system 150 may be communicatively coupled to display 160 and microscope display 170 via I/O device 240. I/O device 240 may facilitate and/or permit processor 210 to communicate data with one or more elements of microscope display 170.

As illustrated, I/O device 240 may be coupled to sensors 250A-250C. For example, a sensor 250 may measure physical phenomena associated with a component of system 100. A sensor 250 may transform a measurement physical phenomena associated with a component of system 100 into digital data. As shown, I/O device 240 may be coupled to a sensor hub 252. As illustrated, sensor hub 252 may be coupled to sensors 250D and 250E. For example, sensor hub 252 may receive data from sensors 250D and 250E and may provide the data from sensors 250D and 250E to I/O device 240. Sensor hub 252 may aggregate data from sensors 250D and 250E and may provide aggregated data from sensors 250D and 250E to I/O device 240. Sensor hub 252 may receive data from sensors 250D and 250E via first protocol and provide the data from sensors 250D and 250E to I/O device 240 via a second protocol, different from the first protocol. Sensor hub 252 may include a microcontroller. For example, the microcontroller may include an ARM Cortex-M (e.g., Cortex-M0, Cortex-M02, Cortex-M1, Cortex-M3, Cortex-M4, Cortex-M7, etc.) microcontroller, an 8051 microcontroller, an AVR (e.g., 8-bit AVR, AVR-32, etc.) microcontroller, a MSP430 microcontroller, a PIC microcontroller, and a Renesas microcontroller, among others.

Figure 2B:
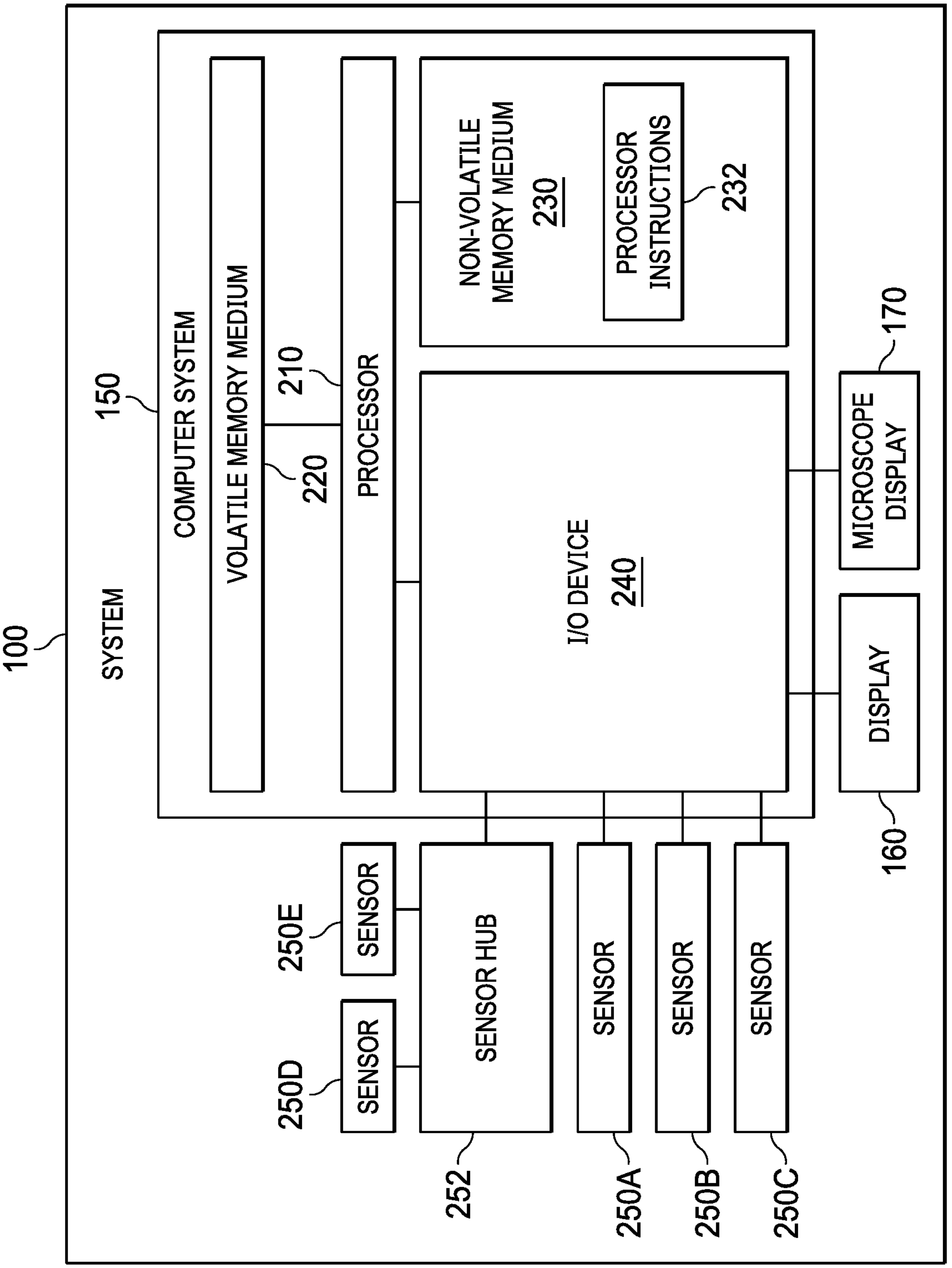
FIG. 2B illustrates another example of a system.

Turning now to FIG. 2B, an example of a system is illustrated. As shown, system 100 may include computer system 150, display 160, microscope display 170, sensors 250A-250E, and sensor hub 252. One or more of sensors 250A-250E may receive information associated with one or more components of system 100. The information associated with one or more components of system 100 may be utilized in determining one or more states of system 100. The information associated with one or more components of system 100 may be utilized in determining one or more issues associated with system 100.

In one example, one or more sensors 250 may monitor a laser of system 100. In a second example, one or more sensors 250 may monitor an amount of energy consumed by a laser of system 100. In a third example, one or more sensors 250 may monitor an amount of energy produced by a laser of system 100. In a fourth example, one or more sensors 250 may monitor an amount of gas of a gas container of system 100. In another example, one or more sensors may monitor how surgeon 110 utilizes a component of system 100.

System 100 may store data from one or more sensors 250 locally. For example, computer system 150 may store data from one or more sensors 250 locally. System 100 may store data from one or more sensors 250 remotely. For example, computer system 150 may provide data from one or more sensors to a remote computer system.

A system may include multiple medical systems 100. Each medical system of the multiple medical systems may include a first component and a first sensor that is configured to determined a first measurement of physical phenomena associated with the first component. In one example, the first sensor may include sensor 250A. In another example, the first sensor may include sensor 250D. A sensor may determine digital data from physical phenomena of a component. For example, the sensor may transform the phenomena of the component into the digital data. The digital data may be a measurement of the phenomena of the component. Each medical system of the multiple medical systems may include a second component and a second sensor that is configured to determined a second measurement of physical phenomena associated with the second component. In one example, the second sensor may include sensor 250B. In another example, the first sensor may include sensor 250E. First multiple measurements of multiple components of respective multiple medical systems 100 may include each first measurement of the physical phenomena associated with each first component of each of the multiple medical systems 100. Second multiple measurements of the multiple components of the respective multiple medical systems 100 may include each second measurement of the physical phenomena associated with each second component of each of the multiple medical systems 100.

Figure 2C:
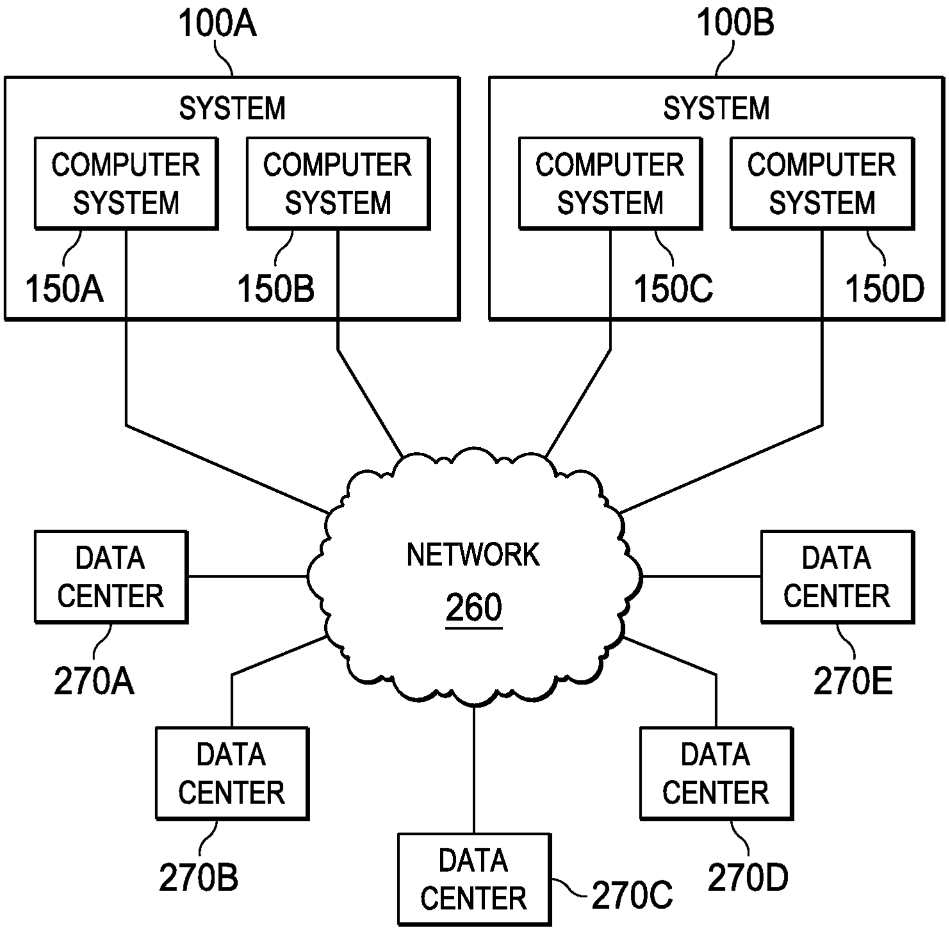
FIG. 2C illustrates an example of computer systems and data centers.

Turning now to FIG. 2C, an example of computer systems and data centers are illustrated. As shown, computer systems 150A-150D may be coupled to a network 260. As illustrated, data centers 270A-270E may be coupled to network 260. A data center 270 may include one or more computer systems. For example, a computer of a data center 270 may include one or more structures and/or one or more functionalities as those described with reference to computer system 150. One or more of computer systems 150A-150D may provide data to one or more of data centers 270A-270E via network 260. For example, one or more of computer systems 250A-250D may provide data from one or more sensors 250 to one or more of data centers 270A-270E via network 260. One or more of computer systems 150A-150D may provide data to one or more of data centers 270A-270E via network 260 in an encrypted fashion. In one example, a computer system 150 may encrypt data from one or more sensors 250 and may provide encrypted data to one or more of data centers 270A-270E via network 260. In another example, a computer system 150 may encrypt data associated with a treatment and may provide encrypted data to one or more of data centers 270A-270E via network 260. One or more of computer systems 150A-150D may receive data from one or more of data centers 270A-270E via network 260. A system may include medical systems 100A and 100B.

Network 260 may include a wired network, a wireless network, an optical network, or a combination of the foregoing, among others. Network 260 may include and/or be coupled to various types of communications networks. For example, network 260 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

One or more of data centers 270A-270E may store data from one or more of computer systems 150A-150D, among others. One or more of data centers 270A-270E may store data from one or more of sensors 250A-250E, among others. One or more of data centers 270A-270E may store data via a database. In one example, the database may include a relational database. In a second example, the database may include a graph database. In another example, the database may include a NoSQL database. One or more of data centers 270A-270E may be utilized in implementing a cloud computing solution. In one example, one or more computer systems of one or more of data centers 270A-270E may be utilized in implementing a cloud computing solution. In another example, one or more virtual machines of one or more computer systems of one or more of data centers 270A-270E may be utilized in implementing a cloud computing solution. One or more of data centers 270A-270E may be utilized in implementing a cloud data storage solution. In one example, a cloud data storage solution may store data from one or more of computer systems 150A-150D, among others. In another example, a cloud data storage solution may store data from one or more of sensors 250A-250E, among others. A cloud data storage solution may store data via a database. In one example, the database may include a relational database. In a second example, the database may include a graph database. In another example, the database may include a NoSQL database.

Figure 3A:
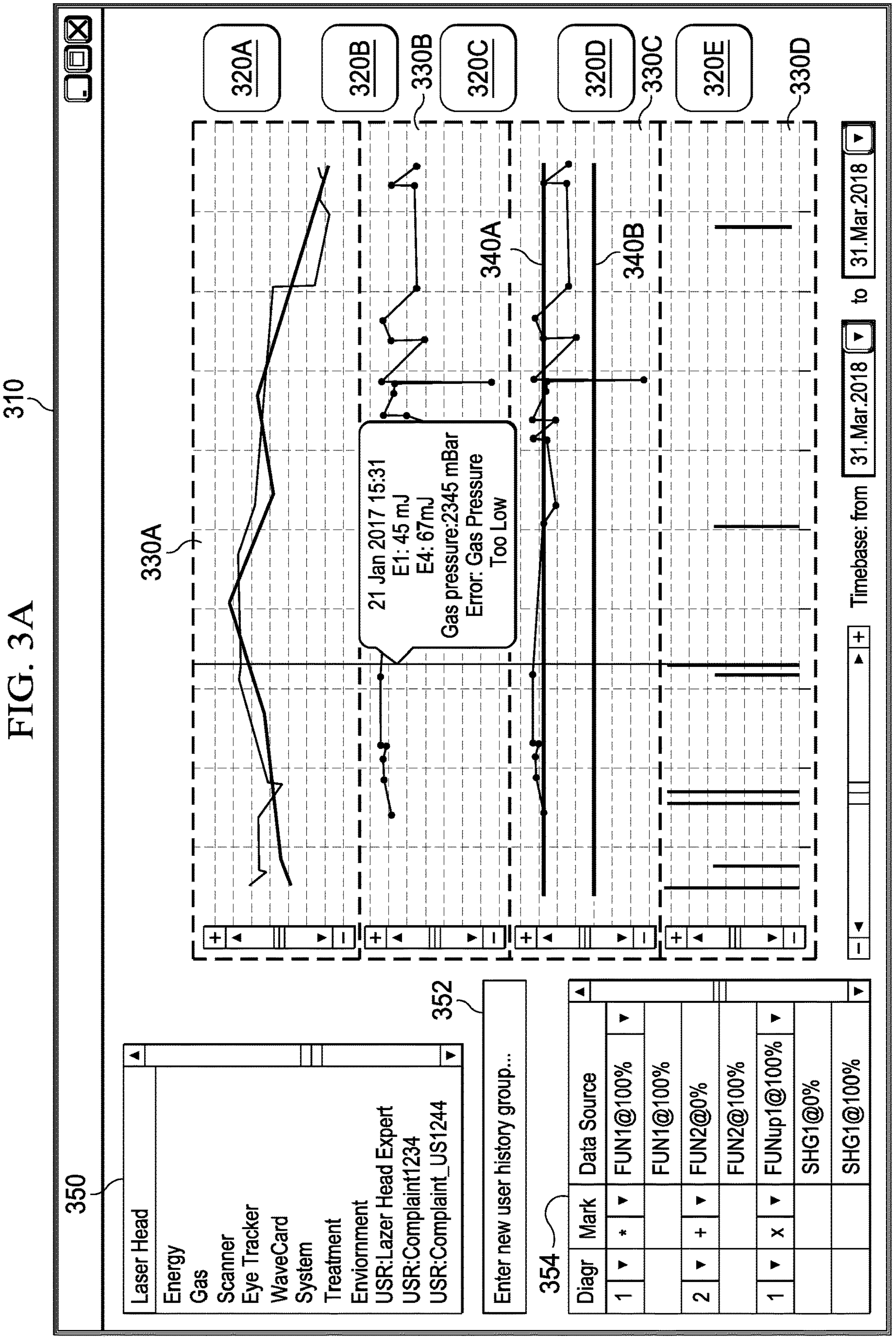
FIG. 3A illustrates an example of a graphical user interface.
Figure 3B:
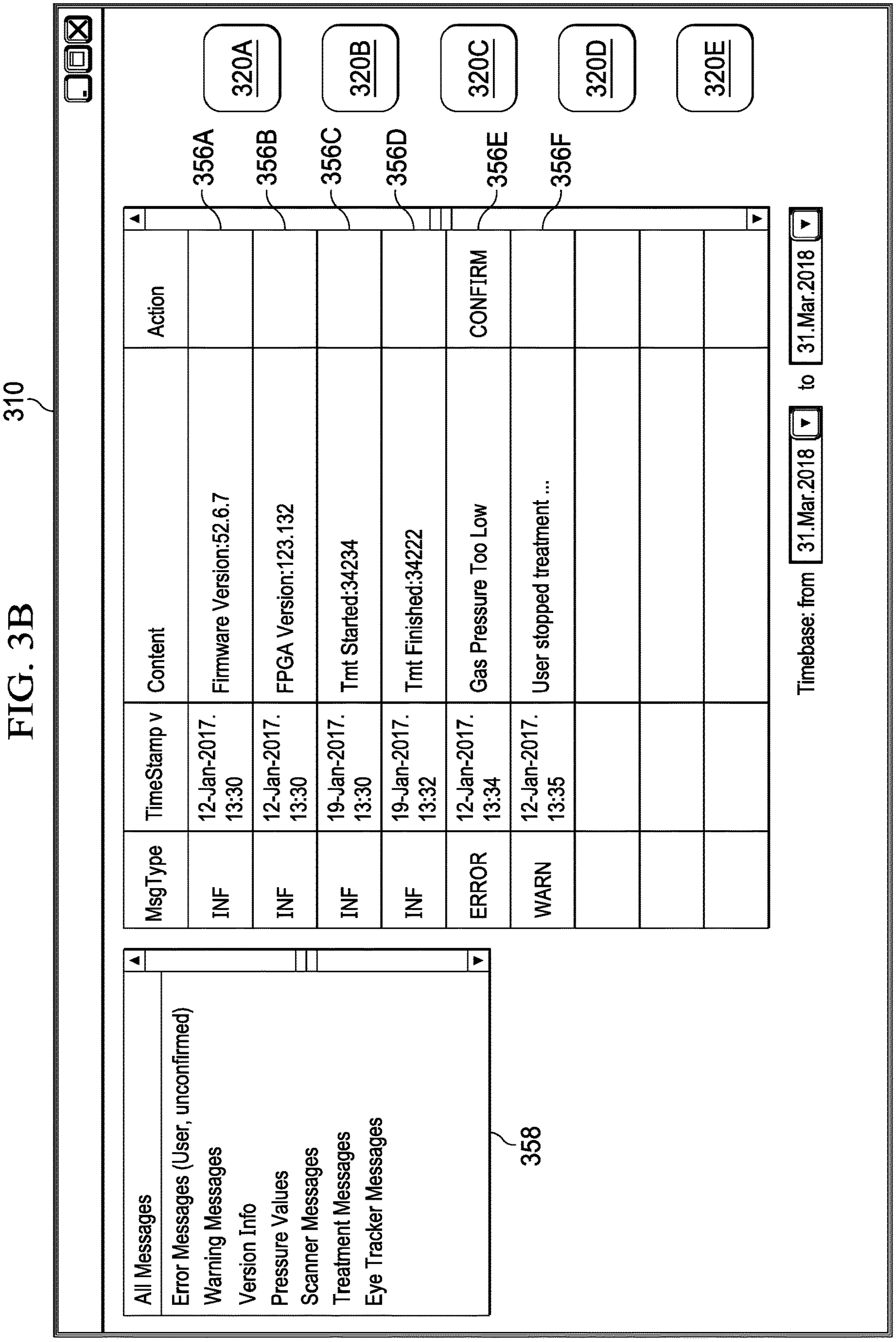
FIG. 3B illustrates a second example of a graphical user interface.

Turning now to FIG. 3A, an example of a graphical user interface is illustrated. As shown, a graphical user interface (GUI) 310 may include icons 320A-320E. An icon of 320A-320E may be selected. In one example, icon 320A may be selected to select a system 100. After icon 320A is selected, system 100A, system 100B, etc. may be selected. A medical facility may be associated with a system 100. In a second example, icon 320B may be selected to view treatment data. FIG. 3B illustrates an example GUI 310 displaying treatment data. In a third example, icon 320C may be selected to select one or more log files. The one or more log files may include data from one or more sensors 250. In a fourth example, icon 320D may be selected to download the one or more log files. In another example, icon 320E may be selected to delete a history group.

As illustrated, GUI areas 330A-330D may present data. In one example, GUI areas 330A-330D may provide report data. The report data may be generated from a search based at least on filter information. In another example, the data presented may be from system 100. The data presented may be from one or more sensors 250 of system 100. In one example, GUI area 330 may present data from a sensor 250 of system 100. In another example, GUI area 330 may present data from multiple sensors 250 of system 100. As shown, GUI area 330C may include thresholds 340A and 340B. For example, a threshold 340 may be configured. A threshold 340 may be configured from user input. As illustrated, data points may be plotted outside thresholds 340A and 340B. In one example, data points may be plotted outside thresholds 340A and 340B may indicate one or more issues associated with system 100. In another example, data points may be plotted outside thresholds 340A and 340B may indicate one or more issues associated with surgeon 110.

As shown, GUI 310 may include a selection menu 350. For example, selection menu 350 may include history groups. A history group may be selected in categorizing data from sensors 250 of system 100. In the example illustrated, a history group of "Laser Head" may have been selected. As illustrated, GUI 310 may include a text input box 352. For example, text input box 352 may be utilized to input text. As shown, GUI 310 may include dropdown menus 354. For example, a dropdown menu may be selected. A selected dropdown menu may indicate data to be presented via a GUI area 330.

GUI 310 may include a web browser. For example, GUI 310 may include a front-end to a web-based application. The web-based application may be implemented via one or more computer systems of one or more data centers 270. The web-based application may be implemented via a cloud computing solution.

GUI 310 may be utilized by a user to monitor a system 100. For example, system 100 may include numerous sensors that provide data associated with system 100. GUI 310 may provide the data associated with system 100 in a fashion that may be discernable by the user. In one example, the user may discern one or more issues associated with system 100. The data associated with system 100 may be correlated with one or more issues associated with system 100. In another example, the user may discern one or more issues associated with surgeon 110. The data associated with system 100 may be correlated with one or more issues associated with surgeon 110.

An artificial intelligence (AI) may utilize data from sensors 250. The AI may learn based at least on data from sensors 250 and based at least on a response of a user to the data from sensors 250. For example, the AI learning may be supervised based at least on the data from sensors 250 and based at least on the response of the user to the data from sensors 250. After the AI learns, the AI may determine one or more issues associated with a system 100 and/or a surgeon 110. The AI may provide information based at least on the one or more issues associated with a system 100 and/or a surgeon 110. For example, the information provided by the AI may include one or more alerts associated with the one or more issues.

The AI may perform one or more actions based at least on the one or more issues associated with a system 100 and/or a surgeon 110. In one example, the AI may issue a service order associated with a system 100. In a second example, the AI may issue a preventative maintenance order associated with a system 100. In a third example, the AI may issue a warning associated with a system 100. In another example, the AI may cease operations of one or more components of a system 100.

Turning now to FIG. 3B, a second example of a graphical user interface is illustrated. As shown, GUI 310 may include icons 320A-320E. As illustrated, GUI 310 may include messages 356A-356F. For example, a message 356 may be associated with a medical treatment. The medical treatment may have been provided in association with a system 100. As shown, GUI 310 may include a message categorization menu 358. For example, GUI 310 may display messages based at least on a message category selected from message categorization menu 358.

Figure 3C:
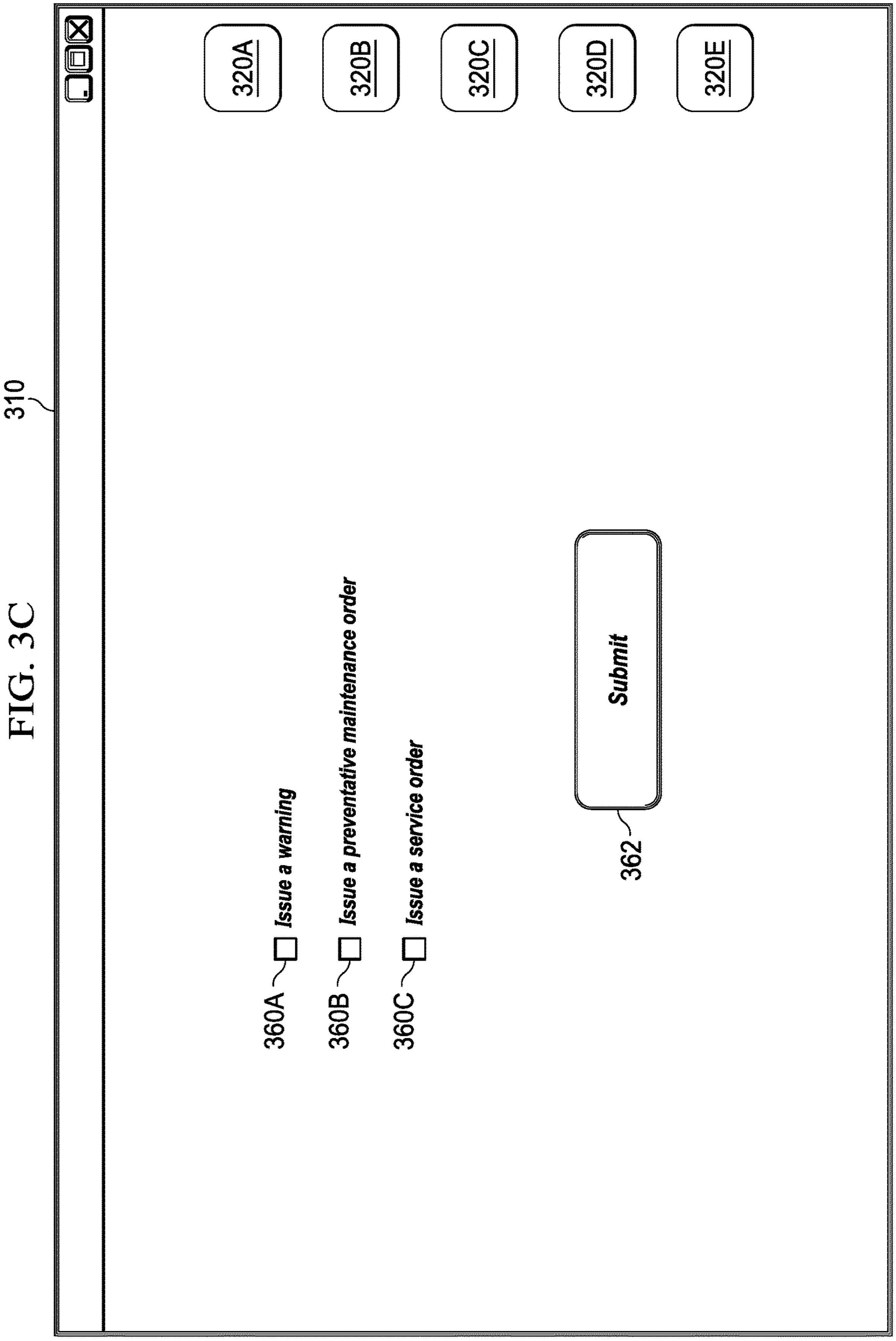
FIG. 3C illustrates another example of a graphical user interface.

Turning now to FIG. 3C, another example of a graphical user interface is illustrated. As illustrated, GUI 310 may include selection areas 360A-360C. For example, selection areas 360A-360C may be check boxes. A user may select selection area 360A to issue a warning associated with a system 100. A user may select selection area 360B to issue a preventative maintenance order associated with a system 100. A user may select selection area 360C to issue a service order associated with a system 100. A user may select a submit icon 362 to execute an issuance associated with one or more of selected selection areas 360A-360C.

One or more thresholds may be determined based at least on one or more of selected selection areas 360A-360C. For example, report data may be correlated with the at least on one or more of selected selection areas 360A-360C to determine one or more thresholds. An AI may correlate the report data with the at least on one or more of selected selection areas 360A-360C to determine one or more thresholds. For example, the AI may correlate the report data with the at least on one or more of selected selection areas 360A-360C to determine one or more thresholds of sensor data. The AI may learn from user input to determine one or more thresholds of sensor data. For example, the AI may learn from user input to determine one or more thresholds of sensor data and what one or more actions to take in response to the sensor data in relation to the one or more thresholds. For example, the AI may utilize supervised machine learning to determine one or more thresholds of sensor data and what one or more actions to take in response to the sensor data in relation to the one or more thresholds.

Figure 4A:
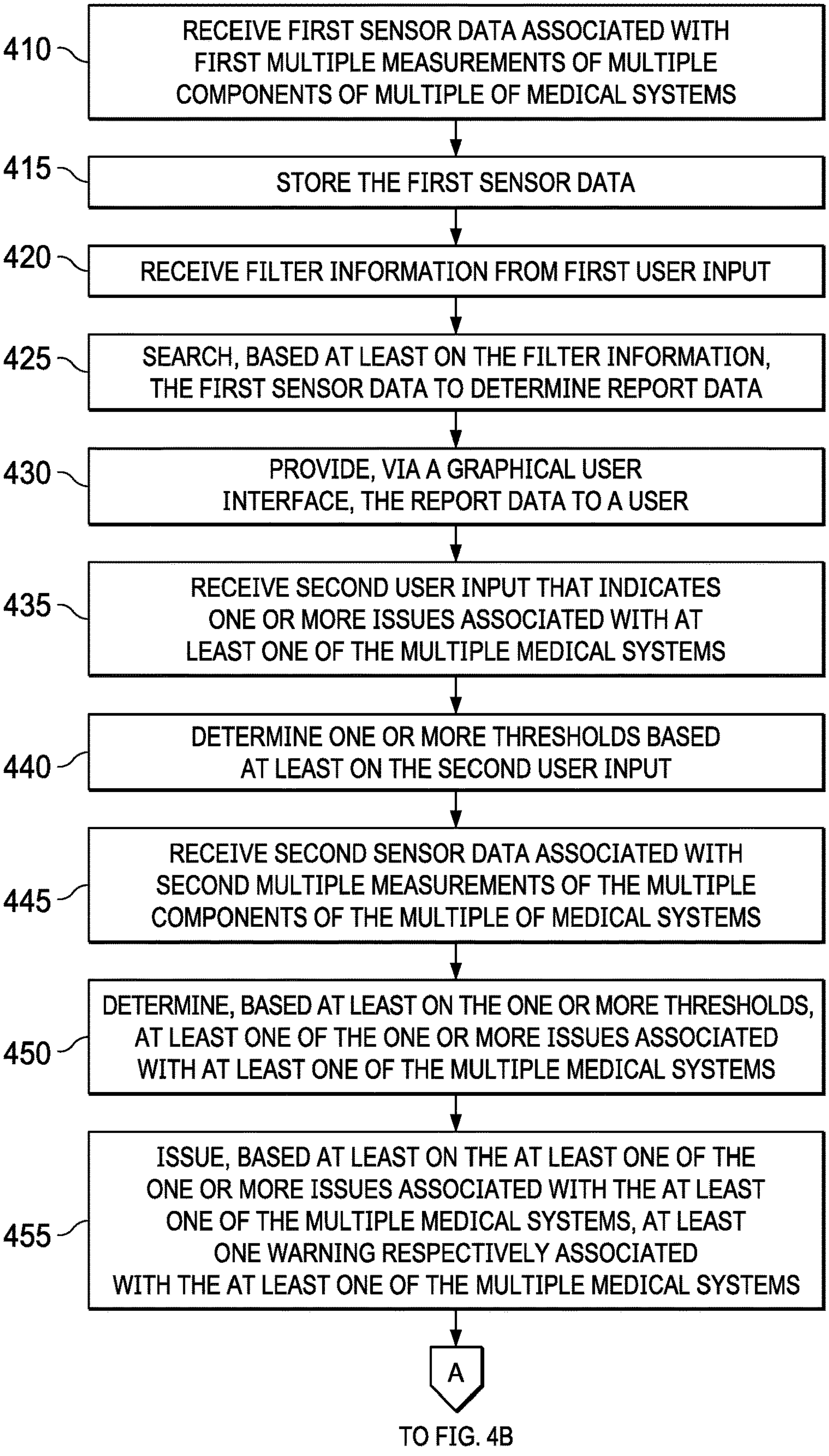
FIGS. 4A and 4B illustrate an example of a method of operating a system.
Figure 4B:
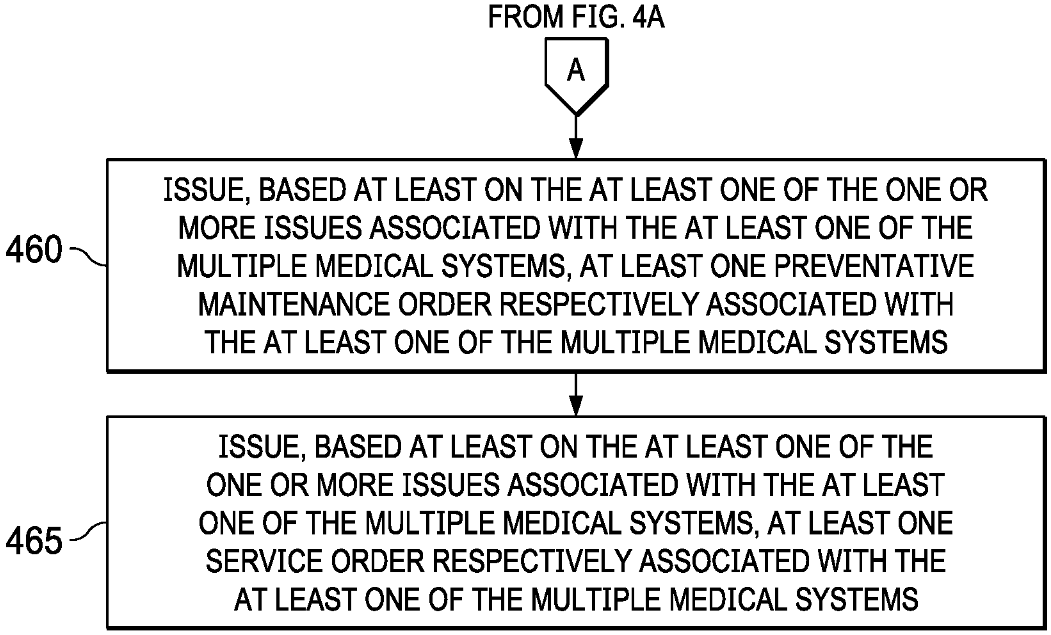

Turning now to FIGS. 4A and 4B, an example of a method of operating a system is illustrated. At 410, first sensor data associated with first multiple measurements of multiple components of multiple of medical systems may be received. In one example, receiving first sensor data associated with first multiple measurements of multiple components of multiple of medical systems may include a data center receiving the first sensor data associated with the first multiple measurements of the multiple components of the multiple of medical systems. In another example, receiving first sensor data associated with first multiple measurements of multiple components of multiple of medical systems may include one or more computer systems of a data center receiving the first sensor data associated with the first multiple measurements of the multiple components of the multiple of medical systems.

At 415, the first sensor data may be stored. For example, the first sensor data may be stored in a database. At 420, filter information may be received from first user input. For example, filter information may be received from first user input via a graphical user interface. At 425, the first sensor data may be searched, based at least on the filter information, to determine report data. For example, searching, based at least on the filter information, the first sensor data to determine the report data may include searching the database to determine the report data.

At 430, the report data may be provided, via a graphical user interface, to a user. For example, providing, via the graphical user interface, the report data to the user may include providing at least a portion of a web-based application to the user. At 435, second user input that indicates one or more issues associated with at least one of the multiple medical systems may be received. At 440, one or more thresholds based at least on the second user input may be determined. At 445, second sensor data associated with second multiple measurements of the multiple components of the multiple medical systems may be received.

At 450, at least one of the one or more issues associated with at least one of the multiple medical systems may be determined based at least on the one or more thresholds. At 455, at least one warning respectively associated with the at least one of the multiple medical systems may be issued based at least on the at least one of the one or more issues associated with the at least one of the multiple medical systems. In one example, issuing the at least one warning respectively associated with the at least one of the multiple medical systems may include providing information indicating the at least one warning via a display of the at least one of the multiple medical systems. In another example, the at least one warning may be associated with past operation of the at least one of the multiple medical systems by at least one medical personnel. The at least one warning may be associated with past operation of system 100 by surgeon 110. In one example, the at least one warning may be provided to surgeon 110 via display 160. In another example, the at least one warning may be provided to surgeon 110 via microscope display 170.

At 460, at least one preventative maintenance order respectively associated with the at least one of the multiple medical systems may be issued based at least on the at least one of the one or more issues associated with the at least one of the multiple medical systems. At 465, at least one service order respectively associated with the at least one of the multiple medical systems may be issued based at least on the at least one of the one or more issues associated with the at least one of the multiple medical systems.

Figure 5A:
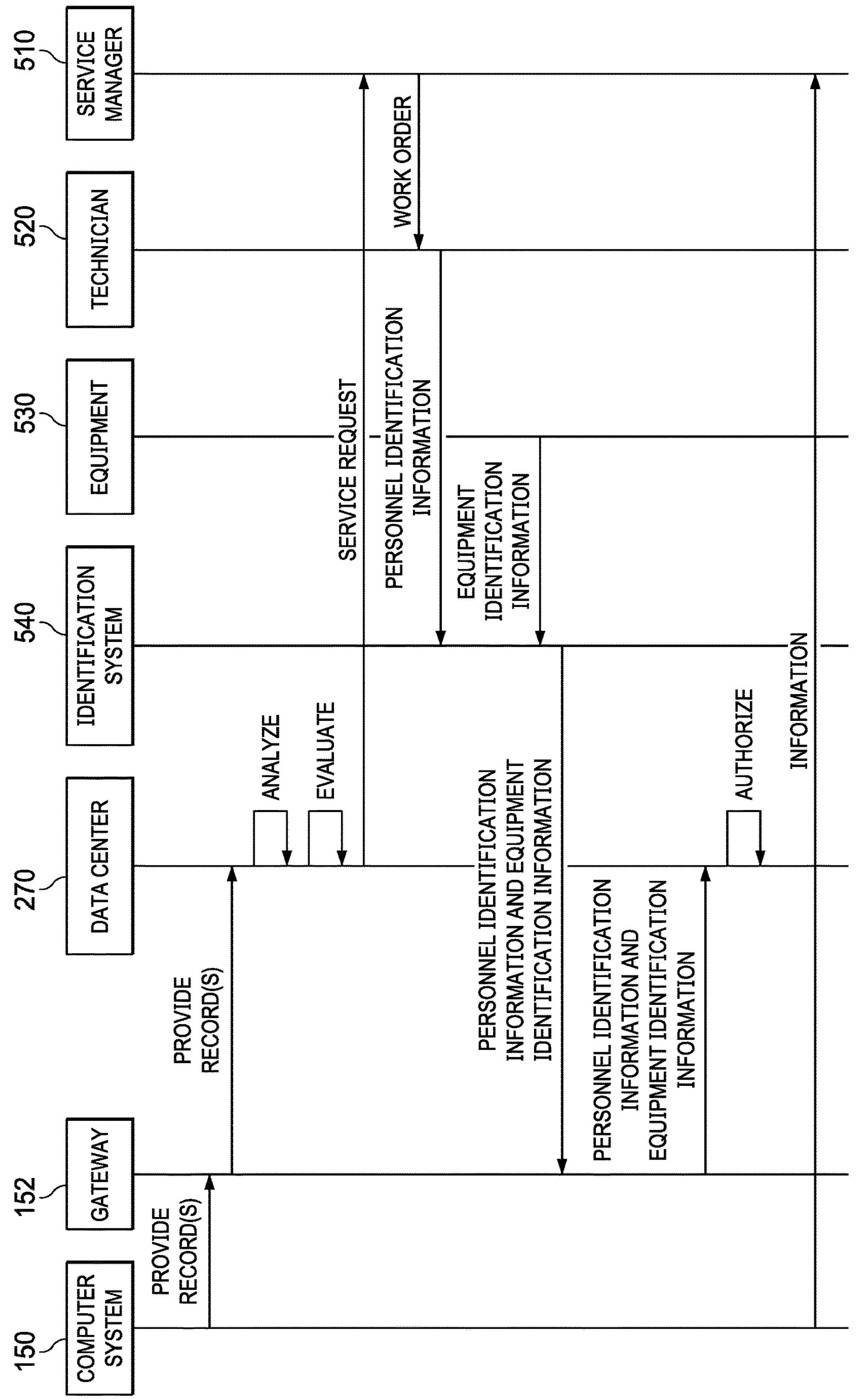
FIG. 5A illustrates an example of a process.

Turning now to FIG. 5A, an example of a process is illustrated. As shown, computer system 150 may provide one or more records to a gateway 152. For example, the one or more records may be or include one or more log files. The one or more log files may be or include sensor data associated with multiple measurements of multiple components of medical system 100. Gateway 152 may be coupled to computer system 150 and to network 260. In one example, gateway 152 may include a network router. For instance, the network router may be configured to be coupled to at least one wide area network. In another example, gateway 152 may include a firewall. Gateway 152 may be or include a bastion host. Gateway 152 may proxy communication between computer system 150 and network 260. For example, gateway 152 may include a proxy server. Gateway 152 may include a WaveNet gateway device, available from Alcon, a division of Novartis AG. Gateway 152 may obtain one or more operation parameters from the one or more records. For example, obtaining the one or more operation parameters from the one or more records may include extracting the one or more operation parameters from the one or more records. Gateway 152 may provide the one or more operation parameters to data center 270.

As illustrated, gateway 152 may provide the one or more records to data center 270. As shown, data center 270 may analyze the one or more records. Data center 270 analyzing the one or more records may include one or more computer systems of data center 270 analyzing the one or more records. In one example, analyzing the one or more records may include determining one or more trends from the one or more records. In another example, analyzing the one or more records may include determining if one or more thresholds are exceeded.

As shown, data center 270 may evaluate the one or more records. Data center 270 evaluating the one or more records may include one or more computer systems of data center 270 evaluating the one or more records. Evaluating the one or more records may include determining a state of medical system 100 from the one or more records. Evaluating the one or more records may include determining one or more services to be performed on medical system 100. In one example, determining the one or more services to be performed on medical system 100 may be based at least on the state of medical system 100. In a second example, determining the one or more services to be performed on medical system 100 may be based at least on the one or more records. In another example, determining the one or more services to be performed on medical system 100 may be based at least on previously received one or more records and/or may be based at least on one or more services that were previously performed on medical system 100. Evaluating the one or more records may include determining a future issue. For example, the future issue may include a future malfunction. The issue may occur if service is not provided to medical system 100 within an amount of time and/or within a number of utilizations of medical system 100.

As illustrated, data center 270 may provide a service request to a service manager 510 (e.g., a person). In one example, providing the service request to service manager 510 may include storing the service request in a database. In another example, providing the service request to service manager 510 may include providing an email to service manager 510. As shown, service manager 510 may provide a work order to a technician 520 (e.g., a person). For example, the work order may be based at least on the service request from data center 270.

As illustrated, technician 520 may provide personnel identification information to an identification system 540. In one example, data center 520 may authenticate the personnel identification information. In another example, identification system 540 may authorize technician 520 based at least on the personnel identification information. Identification system 540 may include a radio frequency identification (RFID) reader. For example, the RFID reader may receive the personnel identification information from a RFID card or a RFID device of technician 520. Identification system 540 may include an optical scanner. For example, the optical scanner may scan a bar code (e.g., a single dimension bar code, a multidimensional bar code, etc.), which may include the personnel identification information.

Identification system 540 may be proximate to medical system 100. In one example, identification system 540 may be located in the same office as medical system 100, or closer. In another example, identification system 540 may be located in the same building as medical system 100, or closer. Identification system 540 may be communicatively coupled to gateway 152.

As shown, identification system 540 may receive equipment identification information associated with equipment 530. In one example, identification system 540 may authenticate the equipment identification information. In another example, identification system 540 may authorize technician 520 based at least on the equipment identification information. For example, the RFID reader may receive the equipment identification information from a RFID card or a RFID device of equipment 530. Identification system 540 may include an optical scanner. For example, the optical scanner may scan a bar code (e.g., a single dimension bar code, a multidimensional bar code, etc.), which may include the equipment identification information.

As illustrated, identification system 540 may provide the personnel identification information and the equipment identification information to gateway 152. As shown, gateway 152 may provide the personnel identification information and the equipment identification information to data center 270. As illustrated, data center 270 may authorize technician 520 to provide service to medical system 100. In one example, data center 270 may authorize technician 520 to provide service to medical system 100 based at least on the personnel identification information associated with technician 520. In a second example, data center 270 may authorize technician 520 to provide service to medical system 100 based at least on one or more qualifications of technician 520. In a third example, data center 270 may authorize technician 520 to provide service to medical system 100 based at least on the one or more qualifications of technician 520 being up to date. In another example, data center 270 may authorize technician 520 to provide service to medical system 100 based at least on the equipment identification information.

Data center 270 may store information associated with equipment 530. In one example, the information associated with equipment 530 may indicate if equipment 530 may be utilized for a service to be performed to medical system 100. In a second example, the information associated with equipment 530 may indicate if equipment 530 has been correctly calibrated to be utilized for a service to be performed to medical system 100. In a third example, the information associated with equipment 530 may indicate if equipment 530 has been correctly calibrated within an amount of time transpiring. In another example, the information associated with equipment 530 may indicate a date that equipment 530 had last been correctly calibrated.

As shown, computer system 150 may provide information to service manager 510. In one example, the information provided to service manager 510 may indicate if technician 520 is authorized to provide service to medical system 100. Technician 520 may or may not be authorized to provide service to medical system 100. In a second example, the information provided to service manager 510 may indicate if equipment 530 is authorized to be utilized in providing service to medical system 100. Equipment 530 may or may not be authorized to be utilized in providing service to medical system 100. In another example, the information provided to service manager 510 may indicate that one or more service procedures have commenced.

After technician 520 and equipment 530 have been authorized to provide service to medical system 100, technician 520 may access and/or download, from data center 270, service instructions associated with medical system 100. For example, data center 270 may implement access control of the service instructions associated with medical system 100.

Figure 5B:
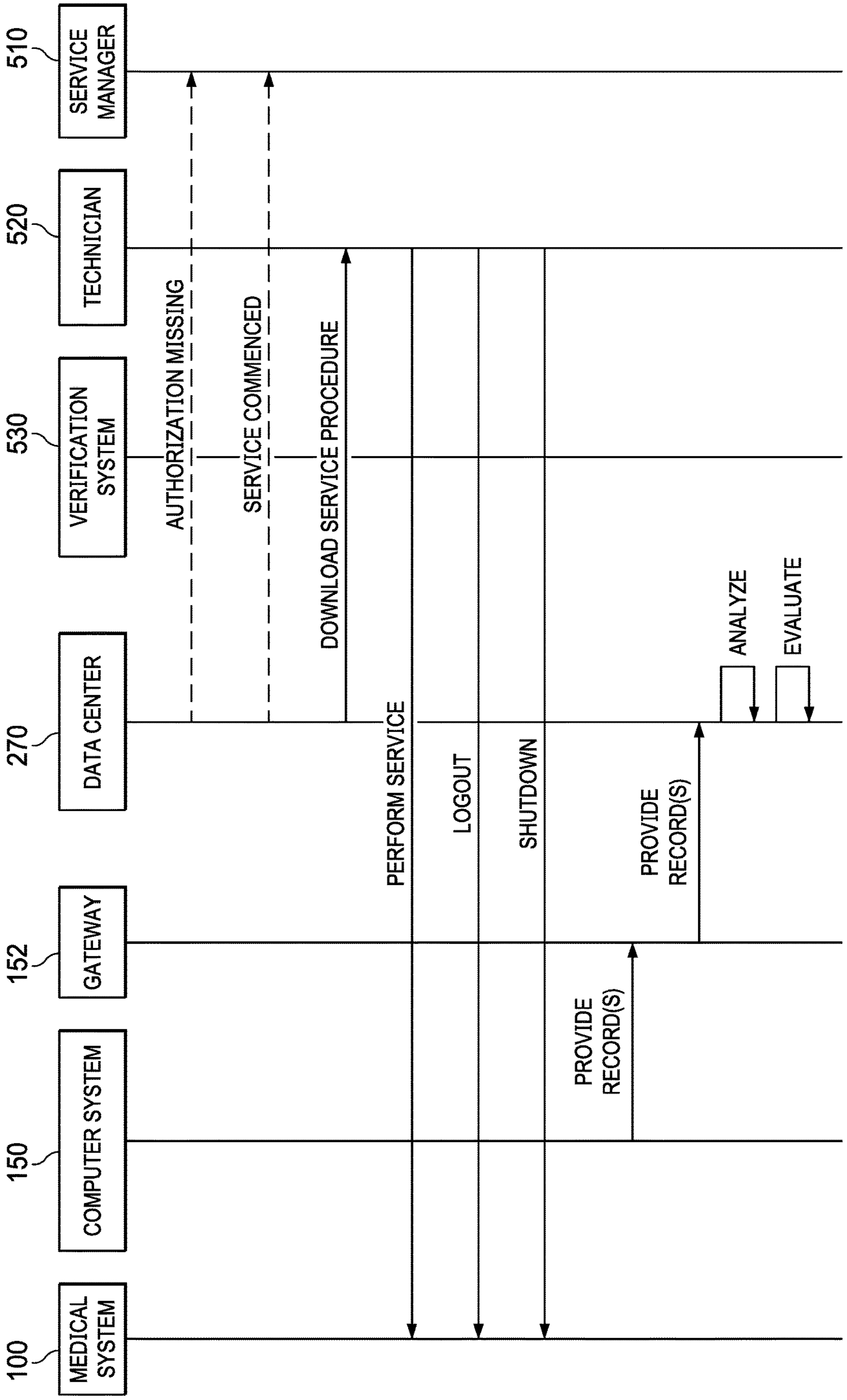
FIG. 5B illustrates a second example of a process.

Turning now to FIG. 5B, a second example of a process is illustrated. As shown, data center 270 may provide, to service manager 510, information that indicates that authorization is missing. In one example, providing the information that indicates that authorization is missing to service manager 510 may include storing the information that indicates that authorization is missing in a database. In another example, providing information that indicates that authorization is missing to service manager 510 may include providing an email, which includes the information that indicates that authorization is missing, to service manager 510.

As illustrated, data center 270 may provide, to service manager 510, information that indicates that service of medical system 100 has commenced. In one example, providing the information that indicates that service of medical system 100 has commenced to service manager 510 may include storing the information that indicates that service of medical system 100 has commenced in a database. In another example, providing information that indicates that service of medical system 100 has commenced is missing to service manager 510 may include providing an email, which includes the information that indicates that service of medical system 100 has commenced, to service manager 510. If data center 270 provides, to service manager 510, information that indicates that authorization is missing, data center 270 may not provide, to service manager 510, information that indicates that service of medical system 100 has commenced. For example, data center 270 may provide, to service manager 510, information that indicates that service of medical system 100 has commenced after technician 520 is authorized to provide service to medical system 100.

As shown, technician 520 may download service procedure information from data center 270. For example, a computer system associated with technician 520 may download service procedure information from data center 270. Data center 270 may provide the service procedure information to the computer system associated with technician 520 after technician 520 is authorized to provide service to medical system 100.

As illustrated, technician 520 may perform service to medical system 100. For example, technician 520 may perform individual service instructions from the service procedure information. Computer system 150 may record performance of the individual service instructions. For example, computer system 150 may store the performance of the individual service instructions via a log file and/or a database.

As shown, technician 520 may logout from medical system 100. For example, technician 520 may logout from medical system 100 after technician 520 performs service to medical system 100. Logging out from medical system 100 may include logging out from computer system 150. Logging out from medical system 100 may include removing a service card from medial system 100.

As shown, technician 520 may shutdown medical system 100. For example, technician 520 may restart medical system 100. Medical system 100 may be restarted after technician 520 performs service to medical system 100. Medical system 100 may initiate providing one or more records to gateway 152 after medical system is restarted and/or is shut down. Technician 510 may remove a service card from medical system 100 after technician 510 shuts down medical system 100.

As illustrated, computer system 150 may provide one or more records to gateway 152. For example, the one or more records may be or include one or more log files. The one or more log files may be or include sensor data associated with multiple measurements of multiple components of medical system 100. Gateway 152 may obtain one or more operation parameters from the one or more records. For example, obtaining the one or more operation parameters from the one or more records may include extracting the one or more operation parameters from the one or more records. Gateway 152 may provide the one or more operation parameters to data center 270. The one or more records may include information associated with the service that technician 520 provided. For example, the one or more records may include diagnostic information and/or evaluation information associated with medical system 100 after technician 520 has performed service to medical system 100.

As shown, gateway 152 may provide the one or more records to data center 270. As illustrated, data center 270 may analyze the one or more records. Data center 270 analyzing the one or more records may include one or more computer systems of data center 270 analyzing the one or more records. In one example, analyzing the one or more records may include determining one or more trends from the one or more records. In another example, analyzing the one or more records may include determining if one or more thresholds are exceeded.

As shown, data center 270 may evaluate the one or more records. Data center 270 evaluating the one or more records may include one or more computer systems of data center 270 evaluating the one or more records. Evaluating the one or more records may include determining a state of medical system 100 from the one or more records.

Evaluating the one or more records may include determining if the one or more services that were performed on medical system 100 resolved one or more issues associated with medical system 100. For example, evaluating the one or more records may include determining if the one or more services that were performed on medical system 100 were performed correctly. Evaluating the one or more records may include determining if the one or more services that were performed on medical system 100 created one or more new issues associated with medical system 100.

Evaluating the one or more records may include determining one or more services to be performed on medical system 100. In one example, determining the one or more services to be performed on medical system 100 may be based at least on the state of medical system 100. In a second example, determining the one or more services to be performed on medical system 100 may be based at least on the one or more records. In another example, determining the one or more services to be performed on medical system 100 may be based at least on previously received one or more records and/or may be based at least on one or more services that were previously performed on medical system 100. Evaluating the one or more records may include determining a future issue. For example, the future issue may include a future malfunction. The issue may occur if service is not provided to medical system 100 within an amount of time and/or within a number of utilizations of medical system 100.

Figure 5C:
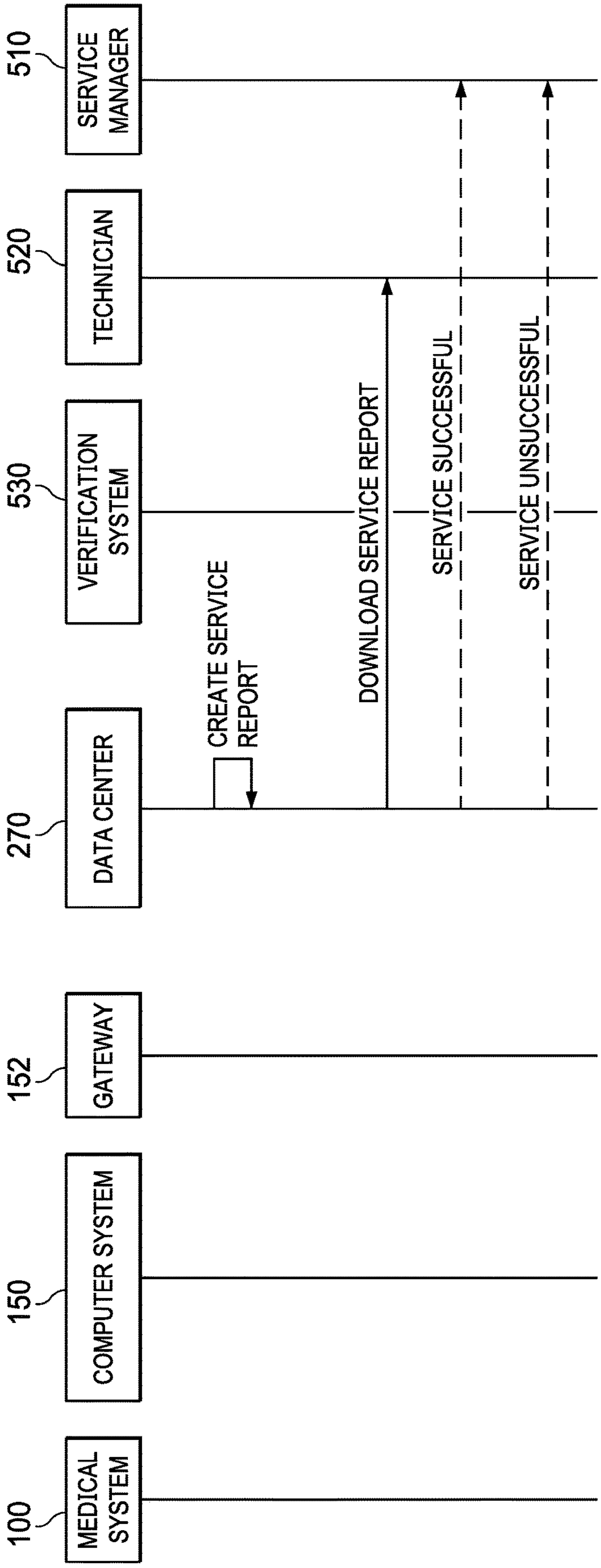
FIG. 5C illustrates another example of a process.

Turning now to FIG. 5C, another example of a process is illustrated. As shown, data center 270 may create a service report. For example, data center 270 may store the service report via a file and/or a database. As illustrated, technician 520 may download the service report. For example, a computer system associated with technician 520 may download the service report. Data center 270 may provide the service report after data center 270 evaluates the one or more records from computer system 150, after service is performed on medical system 100. The service report may include an identification of technician 520 and/or one or more identifications of one or more respective tools utilized in providing service to medical system 100.

As shown, data center 270 may provide, to service manager 510, information that indicates that service was successfully provided to medical system 100. In one example, providing the information that indicates that service was successfully provided to medical system 100 to service manager 510 may include storing the information that indicates that service was successfully provided to medical system 100 in a database. In another example, providing information that indicates that service was successfully provided to medical system 100 to service manager 510 may include providing an email, which includes the information that indicates that service was successfully provided to medical system 100, to service manager 510.

As illustrated, data center 270 may provide, to service manager 510, information that indicates that service was not successfully provided to medical system 100. In one example, providing the information that indicates that service was not successfully provided to medical system 100 to service manager 510 may include storing the information that indicates that service was not successfully provided to medical system 100 in a database. In another example, providing the information that indicates that service was not successfully provided to medical system 100 to service manager 510 may include providing an email, which includes the information that indicates that service was not successfully provided to medical system 100, to service manager 510. If data center 270 may provides, to service manager 510, information that indicates that service was successfully provided to medical system 100, data center data center 270 may not provide, to service manager 510, information that indicates that service was not successfully provided to medical system 100. For example, data center 270 may provide, to service manager 510, information that indicates that service was not successfully provided to medical system 100 after service to medical system 100 was unsuccessful.

Figure 6A:
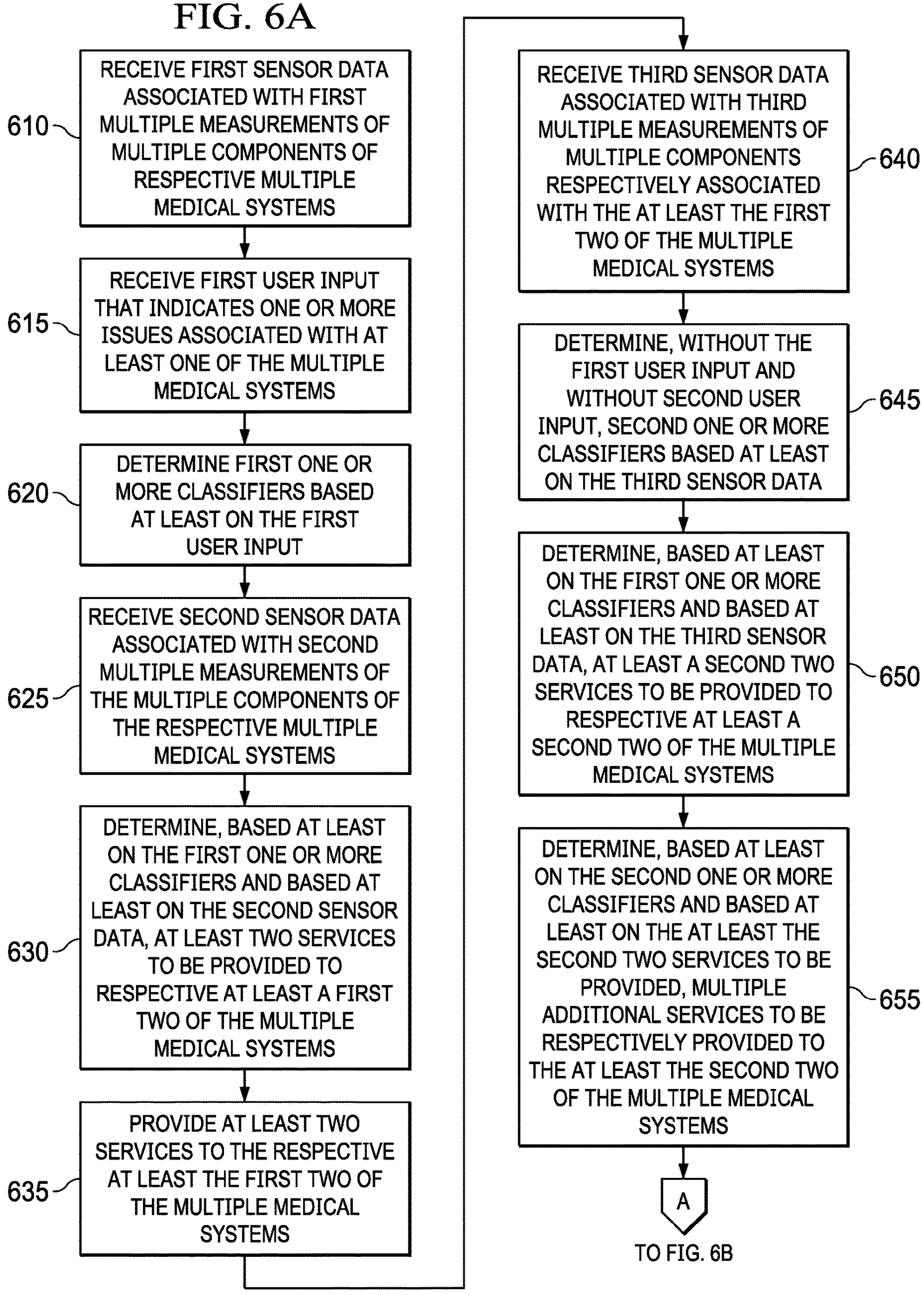
FIGS. 6A and 6B illustrates an example of a method of operating a system.
Figure 6B:
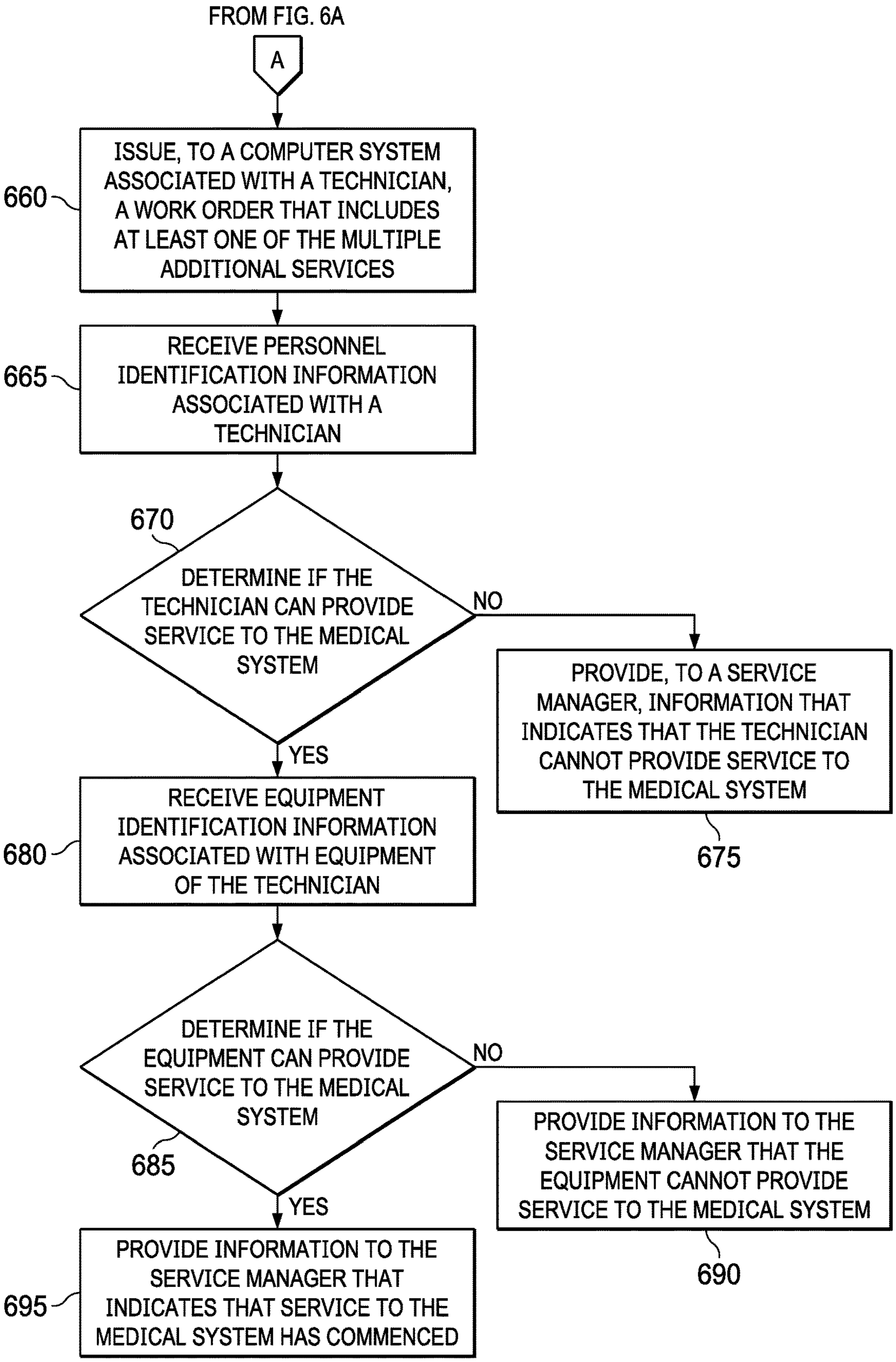

Turning now to FIGS. 6A and 6B, an example of a method of operating a system is illustrated. At 610, first sensor data associated with first multiple measurements of multiple components of respective multiple medical systems. In one example, receiving first sensor data associated with first multiple measurements of multiple components of multiple medical systems may include a data center receiving the first sensor data associated with the first multiple measurements of the multiple components of the multiple medical systems. In another example, receiving first sensor data associated with first multiple measurements of multiple components of multiple medical systems may include one or more computer systems of a data center receiving the first sensor data associated with the first multiple measurements of the multiple components of the multiple medical systems.

At 615, first user input that indicates one or more issues associated with at least one of the multiple medical systems may be received. At 620, first one or more classifiers may be determined based at least on the first user input. A classifier may include a mapping that may utilize pattern matching to determine a closest match. A classifier may be tuned based at least on a data set. For example, a classifier may be tuned based at least on the first user input. In supervised machine learning, a pattern may belong to a class. For example, a class may be characterized as a decision to be made. A classifier may be trained in one or more ways. A classifier may be trained via one or more statistical and/or machine learning processes. For example, classifier may include one or more of a decision tree, a neural network, a k-nearest neighbor process, a kernel method (e.g., a support vector machine), a Gaussian mixture model, and a Bayes classifier, among others. A classifier may be trained based at least on the first sensor data and/or based at least on the first user input.

At 625, second sensor data associated with second multiple measurements of the multiple components of the respective multiple medical systems may be received. At 630, at least two services to be provided to respective at least a first two of the multiple medical systems may be determined based at least on the first one or more classifiers and based at least on the second sensor data.

At 635, the at least two services may be provided to the respective at least the first two of the multiple medical systems. For example, one or more technicians 520 may provide the at least two services to the respective at least the first two of the multiple medical systems. A single technician 520 may provide the at least two services to the respective at least the first two of the multiple medical systems. Multiple technicians 520 may provide the at least two services to the respective at least the first two of the multiple medical systems. At 640, third sensor data associated with third multiple measurements of multiple components respectively associated with the at least the first two of the multiple medical systems may be received.

At 645, second one or more classifiers may be determined, based at least on the third sensor data, without the first user input and without second user input. A data center may determine, based at least on the third sensor data, second one or more classifiers without the first user input and without second user input. For example, one or more computer systems of the data center may determine, based at least on the third sensor data, second one or more classifiers without the first user input and without second user input. Determining, based at least on the third sensor data, second one or more classifiers without the first user input and without second user input may include unsupervised learning. For example, determining the second one or more classifiers from the at least on the third sensor data and without second user input may include utilizing unsupervised machine learning. The second one or more classifiers may be new classifiers. In one example, at least one of the second one or more classifiers may be different from at least one of the first one or more classifiers. In another example, each of the second one or more classifiers may be different from each of the first one or more classifiers. At 650, at least two services to be provided to respective at least a second two of the multiple medical systems may be determined based at least on the first one or more classifiers and based at least on the third sensor data. The at least one of the second two of the multiple medical systems may include the at least one of the first two of the multiple medical systems. The at least one of the second two of the multiple medical systems may not include the at least one of the first two of the multiple medical systems.

At 655, multiple additional services to be respectively provided to the at least the second two of the multiple medical systems may be determined based at least on the second one or more classifiers and based at least on the at least the second two services to be provided. An additional service to be provided to a medical system may be learned from past services provided to medical system. For example, if a first service was provided to a medical system, a second service may need to be provided to the medical system. The second service may need to be provided to the medical system at the time of providing the first service. The second service may need to be provided to the medical system after providing the first service.

For example, the first service may cause an issue after an amount of time transpiring after the first service was performed. The first service may replace a first component of a medical system with a new first component. The new first component may cause a second component to acquire one or more issues and/or fail after an amount of time transpiring after the new first component was installed. For example, an additional service to be provided to a medical system may include replacing the second component with a new second component when the first component is replaced. The additional service may be or include a preventative maintenance.

At 660, a work order that includes at least one of the multiple additional services may be issued to a computer system associated with a technician. At 665, personnel identification associated with a technician may be received. For example, a data center may receive personnel identification associated with a technician. Receiving the personnel identification associated with the technician may include receiving a RFID associated with the technician. Receiving the personnel identification associated with the technician may include receiving a barcode associated with the technician.

At 670, it may be determined if the technician can provide service to the medical system. For example, determining if the technician can provide service to the medical system may be based at least one the personnel identification associated with the technician. The personnel identification associated with the technician may be utilized in determining if the technician has one or more qualifications that may be requisite for the technician to provide service to the medical system. The identification associated with the technician may be utilized in determining if the technician has one or more certifications that may be requisite for the technician to provide service to the medical system. For example, determining if the technician can provide service to the medical system may include retrieving qualification information associated with the technician and/or retrieving certification information associated with the technician, among others, from a memory device and/or a database, among others.

If the technician cannot provide service to the medical system, information that indicates that the technician cannot provide service to the medical system may be provided to a service manager, at 675. If the technician can provide service to the medical system, equipment identification information associated with equipment of the technician may be received at 680.

At 685, it may be determined if the equipment of the technician can provide service to the medical system. For example, determining if the equipment can provide service to the medical system may be based at least one the equipment identification associated with the equipment of the technician. The equipment identification information may be utilized in determining if the equipment has one or more qualifications that may be requisite for the equipment to be utilized to provide service to the medical system. The equipment identification information may be utilized in determining if the equipment has one or more certifications that may be requisite for the equipment to be utilized to provide service to the medical system. For example, determining if the equipment can provide service to the medical system may include retrieving qualification information associated with the equipment and/or retrieving certification information associated with the equipment, among others, from a memory device and/or a database, among others.

If the equipment cannot provide service to the medical system, information that indicates that the equipment cannot provide service to the medical system may be provided to the service manager, at 690. If the equipment can provide service to the medical system, information that indicates that service to the medical system has commenced may be provided to the service manager, at 695.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system, comprising:

at least one processor; and a memory medium that is coupled to the at least one processor and that includes instructions, when executed by the at least one processor, cause the system to:

receive first digital sensor data from a first sensor, the first digital sensor data associated with a first plurality of measurements of a plurality of components of a respective plurality of medical systems;

receive first user input that indicates one or more maintenance issues associated with at least one of the plurality of medical systems;

determine first one or more classifiers based at least on the first user input and based at least on the first digital sensor data;

utilize machine learning to determine one or more thresholds of the first digital sensor data and to determine one or more actions to take in response to the first digital sensor data in relation to the one or more thresholds;

receive second digital sensor data from a second sensor, the second digital sensor data associated with a second plurality of measurements of the plurality of components of the respective plurality of medical systems;

determine, based at least on the first one or more classifiers and based at least on the second digital sensor data, at least two services to be provided to respective at least a first two of the plurality of medical systems;

after the at least two services have been provided to the at least the first two of the plurality of medical systems:

receive third digital sensor data from a third sensor, the third digital sensor data associated with a third plurality of measurements of the plurality of components respectively associated with the at least the first two of the plurality of medical systems;

utilize machine learning to determine, without the first user input and without second user input, second one or more classifiers based at least on the third digital sensor data, the second one or more classifiers different from the first one or more classifiers;

determine, based at least on the first one or more classifiers and based at least on the third digital sensor data, at least a second two services to be provided to respective at least a second two of the plurality of medical systems;

determine, based at least on the second one or more classifiers and based at least on the at least the second two services to be provided, a plurality of additional services to be respectively provided to the at least the second two of the plurality of medical systems;

issue, to a computer system associated with a technician, a work order that includes at least one of the plurality of additional services;

wherein a medical system of the plurality of medical systems is utilized to perform laser eye surgery involving an eye of a patient; and the instructions further cause the medical system to control utilization of one or more medical instruments to perform the laser eye surgery involving the eye of the patient.

2. The system of claim 1, wherein at least one of the second one or more classifiers includes a neural network.

3. The system of claim 1, wherein at least one of the second one or more classifiers includes a k-nearest neighbor process.

4. The system of claim 1, wherein at least one of the plurality of additional services includes at least one preventative maintenance service.

5. The system of claim 1, wherein the instructions further cause the system to: receive personnel information associated with the technician; determine, based at least on the personnel information associated with the technician, if the technician can provide service to the at least one of the plurality of medical systems; if the technician cannot provide service to the at least one of the plurality of medical systems, provide, to a service manager, information that indicates that the technician cannot provide service to the at least one of the plurality of medical systems; and if the technician can provide service to the at least one of the plurality of medical systems, receive equipment identification information associated with equipment of the technician.

6. The system of claim 5, wherein the instructions further cause the system to:

determine, based at least on the equipment identification information, if the equipment of the technician can provide service to the at least one of the plurality of medical systems;

if the equipment of the technician cannot provide service to the at least one of the plurality of medical systems, provide, to the service manager, information that indicates that the equipment cannot provide service to the at least one of the plurality of medical systems; and if the equipment of the technician can provide service to the at least one of the plurality of medical systems, provide, to the service manager, information that indicates that the service to the at least one of the plurality of medical systems has commenced.

7. The system of claim 5, wherein, to receive the personnel information associated with the technician, the instructions further cause the system to receive at least one of a radio frequency identification (RFID) associated with the technician and a barcode associated with the technician.

8. The system of claim 1, further comprising:

the plurality of medical systems.

9. The system of claim 8, further comprising:

a plurality of gateway devices coupled to the plurality of medical systems, respectively;

wherein the plurality of gateway devices includes a respective plurality of network routers configured to be coupled to at least one wide area network.

10. The system of claim 8, wherein each medical system of the plurality of medical systems includes a first component and the first sensor configured to determine a first measurement of physical phenomena associated with the first component;

wherein each medical system of the plurality of medical systems includes a second component and the second sensor configured to determine a second measurement of physical phenomena associated with the second component;

wherein the first plurality of measurements of the plurality of components of the respective plurality of medical systems includes each first measurement of the physical phenomena associated with each first component of each of the plurality of medical systems; and wherein the second plurality of measurements of the plurality of components of the respective plurality of medical systems includes each second measurement of the physical phenomena associated with each second component of each of the plurality of medical systems.

11. The system of claim 10, wherein each medical system of the plurality of medical systems includes a sensor hub;

wherein the first sensor of each medical system of the plurality of medical systems is coupled to the sensor hub of the medical system; and wherein the sensor hub of each medical system of the plurality of medical systems is configured to receive data from the first sensor of the medical system via a first protocol and provide the data to the computer system via a second protocol.

12. A method, comprising:

receiving first digital sensor data from a first sensor, the first digital sensor data associated with a first plurality of measurements of a plurality of components of a respective plurality of medical systems;

receiving first user input that indicates one or more maintenance issues associated with at least one of the plurality of medical systems;

determining first one or more classifiers based at least on the first user input and based at least on the first digital sensor data;

utilizing machine learning to determine one or more thresholds of the first digital sensor data and to determine one or more actions to take in response to the first digital sensor data in relation to the one or more thresholds;

receiving second digital sensor data from a second sensor, the second digital sensor data associated with a second plurality of measurements of the plurality of components of the respective plurality of medical systems;

determining, based at least on the first one or more classifiers and based at least on the second digital sensor data, at least two services to be provided to respective at least a first two of the plurality of medical systems;

after the at least two services have been provided to the at least the first two of the plurality of medical systems:

receiving third digital sensor data from a third sensor, the third digital sensor data associated with a third plurality of measurements of the plurality of components respectively associated with the at least the first two of the plurality of medical systems;

utilizing machine learning to determine, without the first user input and without second user input, second one or more classifiers based at least on the third digital sensor data, the second one or more classifiers different from the first one or more classifiers;

determining, based at least on the first one or more classifiers and based at least on the third digital sensor data, at least a second two services to be provided to respective at least a second two of the plurality of medical systems;

determining, based at least on the second one or more classifiers and based at least on the at least the second two services to be provided, a plurality of additional services to be respectively provided to the at least the second two of the plurality of medical systems;

issuing, to a computer system associated with a technician, a work order that includes at least one of the plurality of additional services; and causing a medical system of the plurality of medical systems to control utilization of one or more medical instruments to perform laser eye surgery involving an eye of a patient.

13. The method of claim 12, wherein at least one of the second one or more classifiers includes a neural network.

14. The method of claim 12, wherein at least one of the second one or more classifiers includes a k-nearest neighbor process.

15. The method of claim 12, wherein at least one of the plurality of additional services includes at least one preventative maintenance service.

16. The method of claim 12, further comprising: receiving personnel information associated with the technician; determining, based at least on the personnel information associated with the technician, if the technician can provide service to the at least one of the plurality of medical systems; if the technician cannot provide service to the at least one of the plurality of medical systems, providing, to a service manager, information that indicates that the technician cannot provide service to the at least one of the plurality of medical systems; and if the technician can provide service to the at least one of the plurality of medical systems, receiving equipment identification information associated with equipment of the technician.

17. The method of claim 16, further comprising:

determining, based at least on the equipment identification information, if the equipment of the technician can provide service to the at least one of the plurality of medical systems;

if the equipment of the technician cannot provide service to the at least one of the plurality of medical systems, providing, to the service manager, information that indicates that the equipment cannot provide service to the at least one of the plurality of medical systems; and if the equipment of the technician can provide service to the at least one of the plurality of medical systems, providing, to the service manager, information that indicates that the service to the at least one of the plurality of medical systems has commenced.

18. The method of claim 16, wherein the receiving the personnel information associated with the technician includes receiving at least one of a radio frequency identification (RFID) associated with the technician and a barcode associated with the technician.

* * * * *